(12) United States Patent
Penta et al.

(10) Patent No.: US 8,324,165 B2
(45) Date of Patent: Dec. 4, 2012

(54) COMPOSITIONS FOR TREATING ARTHRITIS COMPRISING HG1023575 POLYPEPTIDE

(75) Inventors: Kalyani Penta, Palo Alto, CA (US); Srinivas Kothakota, Pacifica, CA (US); Lewis T. Williams, Mill Valley, CA (US); Kevin Hestir, Kensington, CA (US); Shannon Marshall, Baltimore, MD (US); Jeffrey Finer, Foster City, CA (US); Yan Wang, Redwood City, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 12/992,582

(22) PCT Filed: May 13, 2009

(86) PCT No.: PCT/US2009/043834
§ 371 (c)(1), (2), (4) Date: Apr. 13, 2011

(87) PCT Pub. No.: WO2009/140418
PCT Pub. Date: Nov. 19, 2009

(65) Prior Publication Data
US 2011/0288024 A1    Nov. 24, 2011

Related U.S. Application Data

(60) Provisional application No. 61/053,020, filed on May 14, 2008.

(51) Int. Cl.
*A61P 19/02* (2006.01)
*A61K 38/17* (2006.01)

(52) U.S. Cl. .................. 514/16.8; 514/825; 530/350
(58) Field of Classification Search .................. None
See application file for complete search history.

(56) References Cited

U.S. PATENT DOCUMENTS

2004/0171109 A1    9/2004    Haudenschild et al.
2005/0196754 A1    9/2005    Drmanac et al.

OTHER PUBLICATIONS

Record for GenBank Accession No. AC099685, *Homo sapiens* chromosome 8, clone RP11-87N16, complete sequence, Feb. 22, 2002, 5 pages as printed.*
Liebman et al, Chondrocyte Culture and Assay, pp. 12.2.1-12.2.18 (18 pages total) from Current Protocols in Pharmacology (2001), published by John Wiley & Sons, Inc.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
International Search Report dated Oct. 30, 2009 issued in Application No. PCT/US2009/043834.
International Preliminary Report on Patentability dated Nov. 17, 2010 issued in Application No. PCT/US2009/043834.

* cited by examiner

*Primary Examiner* — Zachary Howard
(74) *Attorney, Agent, or Firm* — Anna L. Barry

(57) ABSTRACT

The invention provides pharmaceutical polypeptide compositions that promote proteoglycan synthesis, and promote the activity of chondrocyte cells, thereby treating arthritis. Methods of providing these compositions to treat arthritis are also provided.

3 Claims, 6 Drawing Sheets

Microscopic examination of cell morphology

*P4: Passage 4*
1C

← *Elongated, fibroblastic morphology*

*P1: Passage 1*
1B

*P0: Primary Culture*
1A

*'Cobblestone' morphology*

Comparison of the Alcian Blue capture method vs. the G-25 column method for analyzing radiolabeled proteoglycans First plate Duplicate plate

SEQUENCE LISTING

<160> NUMBER OF SEQ ID NOS: 12

<210> SEQ ID NO 1
<211> LENGTH: 333
<212> TYPE: DNA

<213> ORGANISM: Mus musculus

<400> SEQUENCE: 1

| atgaggaacc | tactctcacc | actcctcttc | aacatagtac | tggaagtcct | agccagagca | 60 |
| atcagacaaa | agaaggaaat | agaggaaatc | caaatcggta | aagaggaagt | caaactgtca | 120 |
| ctggttgctg | acgatatgac | ctttctcctt | gagaaccta | cggactcctc | tagaaagctc | 180 |
| ctagaactga | taaagaatt | cagcaaagtt | tccagataca | agattaatgg | acacaaatca | 240 |
| gtagctcttc | tatacatcaa | cagctaccaa | gcagagaatc | acatcaagaa | ctcaatccct | 300 |
| tttacaatag | ctgcaaaaaa | caaacaaaaa | taa | | | 333 |

<210> SEQ ID NO 2
<211> LENGTH: 110
<212> TYPE: PRT
<213> ORGANISM: Mus musculus

<400> SEQUENCE: 2

Met Arg Asn Leu Leu Ser Pro Leu Leu Phe Asn Ile Val Leu Glu Val
1               5                   10                  15

Leu Ala Arg Ala Ile Arg Gln Lys Lys Glu Ile Glu Glu Ile Gln Ile
            20                  25                  30

Gly Lys Glu Glu Val Lys Leu Ser Leu Val Ala Asp Asp Met Thr Phe
        35                  40                  45

Leu Leu Glu Asn Pro Thr Asp Ser Ser Arg Lys Leu Leu Glu Leu Ile
    50                  55                  60

Lys Glu Phe Ser Lys Val Ser Arg Tyr Lys Ile Asn Gly His Lys Ser
65                  70                  75                  80

Val Ala Leu Leu Tyr Ile Asn Ser Tyr Gln Ala Glu Asn His Ile Lys
                85                  90                  95

Asn Ser Ile Pro Phe Thr Ile Ala Ala Lys Asn Lys Gln Lys
            100                 105                 110

<210> SEQ ID NO 3
<211> LENGTH: 570
<212> TYPE: DNA
<213> ORGANISM: Mus musculus

<400> SEQUENCE: 3

| atgctggtgt | cctctgagct | gttacattgc | ttaataaagc | tcctcttcgt | cttgctcatc | 60 |
| ctccacttat | ctgcatatct | cgttcttcct | ggtcacagga | ttagaactca | ggacgggacg | 120 |
| aatggcaagg | ctaaaagctg | taacacaaac | agggctgaga | cacgctcctt | gctcgccaag | 180 |
| ttgcaggcga | agggaaggaa | agaagagctg | tggccctta | gggagcccag | acctgggagc | 240 |
| tccccgagcc | agggctatga | cccactcttt | ggggccctgc | ggttcctggc | gtctccaagc | 300 |
| ttctggggc | cactgtgctc | cctggtgcca | gctgtggaag | tgcttgcagt | gcgcctggtc | 360 |
| cagctgcagc | cttatagaga | gcctgcgccc | gggtacgacc | tagagcttcc | taccccactg | 420 |
| cagcaactgg | catgtctgac | tgcgcagtgg | ccgaaccca | ggctcactca | caaacccctc | 480 |
| accactccac | gcagtctccc | ttggcaggcg | tgggattcag | ccagtggcc | tgaattgagc | 540 |
| gcagcctgcc | aggctgagtg | ggtggaatga | | | | 570 |

<210> SEQ ID NO 4
<211> LENGTH: 189
<212> TYPE: PRT
<213> ORGANISM: Mus musculus

<400> SEQUENCE: 4

```
Met Leu Val Ser Ser Glu Leu Leu His Cys Leu Ile Lys Leu Leu Phe
1               5                   10                  15

Val Leu Leu Ile Leu His Leu Ser Ala Tyr Leu Val Leu Pro Gly His
                20                  25                  30

Arg Ile Arg Thr Gln Asp Gly Thr Asn Gly Lys Ala Lys Ser Cys Asn
            35                  40                  45

Thr Asn Arg Ala Glu Thr Arg Ser Leu Leu Ala Lys Leu Gln Ala Lys
        50                  55                  60

Gly Arg Lys Glu Glu Leu Trp Pro Phe Arg Glu Pro Arg Pro Gly Ser
65                  70                  75                  80

Ser Pro Ser Gln Gly Tyr Asp Pro Leu Phe Gly Ala Leu Arg Phe Leu
                85                  90                  95

Ala Ser Pro Ser Phe Trp Gly Pro Leu Cys Ser Leu Val Pro Ala Val
                100                 105                 110

Glu Val Leu Ala Val Arg Leu Val Gln Leu Gln Pro Tyr Arg Glu Pro
            115                 120                 125

Ala Pro Gly Tyr Asp Leu Glu Leu Pro Thr Pro Leu Gln Gln Leu Ala
        130                 135                 140

Cys Leu Thr Ala Gln Trp Pro Asn Pro Arg Leu Thr His Lys Pro Leu
145                 150                 155                 160

Thr Thr Pro Arg Ser Leu Pro Trp Gln Ala Trp Asp Ser Gly Gln Trp
                165                 170                 175

Pro Glu Leu Ser Ala Ala Cys Gln Ala Glu Trp Val Glu
                180                 185

<210> SEQ ID NO 5
<211> LENGTH: 507
<212> TYPE: DNA
<213> ORGANISM: Mus musculus

<400> SEQUENCE: 5
atgaggcttc tcattctcac ctgtcttgtg gctgttgctc ttgccaggcc taaacttcct     60
cttagatacc cagaacgcct tcagaatcca tcagagagca gtgagcctat accattagaa    120
tcaagagagg aatacatgaa tggtatgaac aggcagagaa acattctgag agaaaaacag    180
actgatgaaa tcaagaactg tgttgtggca gagcctgaga gatggaatc cagcatcagt     240 tcatcgagtg aggaacagtt tgtagactg aacgaataca ccaacttca gctgcaagct      300 gcccatgccc aggagcaaat cgcagaatg aatgaaaaca gccatgtcca agtgcctttc     360
cagcagctca ccaacttgc tgcctacccc tatgctgttt ggtactatcc acaaatcatg     420
cagtatgttc ctttcccacc gttttccgac atctccaatc ccactgctca tgaaaattat    480
gaaaaaaata acgtcatgct acagtgg                                        507

<210> SEQ ID NO 6
<211> LENGTH: 169
<212> TYPE: PRT
<213> ORGANISM: Mus musculus

<400> SEQUENCE: 6

Met Arg Leu Leu Ile Leu Thr Cys Leu Val Ala Val Ala Leu Ala Arg
1               5                   10                  15

Pro Lys Leu Pro Leu Arg Tyr Pro Glu Arg Leu Gln Asn Pro Ser Glu
                20                  25                  30

Ser Ser Glu Pro Ile Pro Leu Glu Ser Arg Glu Glu Tyr Met Asn Gly
            35                  40                  45
```

```
Met Asn Arg Gln Arg Asn Ile Leu Arg Glu Lys Gln Thr Asp Glu Ile
            50                  55                  60

Lys Asn Cys Val Val Ala Glu Pro Glu Lys Met Glu Ser Ser Ile Ser
 65                  70                  75                  80

Ser Ser Ser Glu Glu Gln Phe Cys Arg Leu Asn Glu Tyr Asn Gln Leu
                85                  90                  95

Gln Leu Gln Ala Ala His Ala Gln Glu Gln Ile Arg Arg Met Asn Glu
            100                 105                 110

Asn Ser His Val Gln Val Pro Phe Gln Gln Leu Asn Gln Leu Ala Ala
            115                 120                 125

Tyr Pro Tyr Ala Val Trp Tyr Tyr Pro Gln Ile Met Gly Tyr Val Pro
    130                 135                 140

Phe Pro Pro Phe Ser Asp Ile Ser Asn Pro Thr Ala His Glu Asn Tyr
145                 150                 155                 160

Glu Lys Asn Asn Val Met Leu Gln Trp
                165

<210> SEQ ID NO 7
<211> LENGTH: 591
<212> TYPE: DNA
<213> ORGANISM: Mus musculus

<400> SEQUENCE: 7
atggcgcagc tgtgcgggct gaggcggagc cgggcgtttc tcgccctgct gggatcgctg     60
ctcctctctg gggtcctggc ggccgaccga gaacgcagca tccacgactt ctgcctggtg    120
tcgaaggtgg tgggcagatg ccgggcctcc atgcctaggt ggtggtacaa tgtcactgac    180
ggatcctgcc agctgtttgt gtatggggc tgtgacggaa acagcaataa ttacctgacc     240
aaggaggagt gcctcaagaa atgtgccact gtcacagaga atgccacggg tgacctggcc    300
accagcagga atgcagcgga ttcctctgtc ccaagtgctc ccagaaggca ggattctgaa    360
gaccactcca gcgatatgtt caactatgaa gaatactgca ccgccaacgc agtcactggg    420
ccttgccgtg catccttccc acgctggtac tttgacgtgg agaggaactc ctgcaataac    480
tccatggtct acctgatccg ggtggcacgg aggaaccagg agcgtgccct gcgcaccgtc    540
tggagctccg gagatgacaa ggagcagctg gtgaagaaca catatgtcct g              591

<210> SEQ ID NO 8
<211> LENGTH: 197
<212> TYPE: PRT
<213> ORGANISM: Mus musculus

<400> SEQUENCE: 8

Met Ala Gln Leu Cys Gly Leu Arg Arg Ser Arg Ala Phe Leu Ala Leu
 1               5                  10                  15

Leu Gly Ser Leu Leu Leu Ser Gly Val Leu Ala Ala Asp Arg Glu Arg
             20                  25                  30

Ser Ile His Asp Phe Cys Leu Val Ser Lys Val Val Gly Arg Cys Arg
         35                  40                  45

Ala Ser Met Pro Arg Trp Trp Tyr Asn Val Thr Asp Gly Ser Cys Gln
    50                  55                  60

Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
            100                 105                 110
```

Ala Pro Arg Arg Gln Asp Ser Glu Asp His Ser Ser Asp Met Phe Asn
            115                 120                 125

Tyr Glu Glu Tyr Cys Thr Ala Asn Ala Val Thr Gly Pro Cys Arg Ala
            130                 135                 140

Ser Phe Pro Arg Trp Tyr Phe Asp Val Glu Arg Asn Ser Cys Asn Asn
145                 150                 155                 160

Ser Met Val Tyr Leu Ile Arg Val Ala Arg Arg Asn Gln Glu Arg Ala
                165                 170                 175

Leu Arg Thr Val Trp Ser Ser Gly Asp Asp Lys Glu Gln Leu Val Lys
            180                 185                 190

Asn Thr Tyr Val Leu
            195

<210> SEQ ID NO 9
<211> LENGTH: 636
<212> TYPE: DNA
<213> ORGANISM: Mus musculus

<400> SEQUENCE: 9

```
atgaatcctg cggcagaagc cgagttcaac atcctcctgg ccaccgactc ctacaaggtt      60
actcactata acaatatccc acccaacaca agcaaagttt attcctactt tgaatgccgt     120
gaaaagaaga cagaaaactc caaattaagg aaggtgaaat atgaggaaac agtattttat     180
gggttgcagt acattcttaa taagtactta aaaggtaaag tagtaaccaa agagaaaatc     240
caggaagcca agatgtctca aaagaacat ttccaagatg atgtctttaa tgaaaaggga     300
tggaactaca ttcttgagaa gtatgatggg catcttccaa tagaaataaa agctgttcct     360
gagggctttg tcattcccag aggaaatgtt ctcttcacgg tggaaaacac agatccagag     420
tgttactggc ttacaaattg gattgagact attcttgttc agtcctggta tccaatcaca     480
gtggccacaa attctagaga gcagaagaaa atattggcca atatttgtt agaaacttct     540
ggtaacttag atggtctgga atacaagtta catgattttg ctacagagg agtctcttcc     600
caagagtacc ataacagctt gggggaaaga ccatga                              636
```

<210> SEQ ID NO 10
<211> LENGTH: 211
<212> TYPE: PRT
<213> ORGANISM: Mus musculus

<400> SEQUENCE: 10

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

```
Asn Val Leu Phe Thr Val Glu Asn Thr Asp Pro Glu Cys Tyr Trp Leu
    130                 135                 140
Thr Asn Trp Ile Glu Thr Ile Leu Val Gln Ser Trp Tyr Pro Ile Thr
145                 150                 155                 160
Val Ala Thr Asn Ser Arg Glu Gln Lys Lys Ile Leu Ala Lys Tyr Leu
                165                 170                 175
Leu Glu Thr Ser Gly Asn Leu Asp Gly Leu Glu Tyr Lys Leu His Asp
            180                 185                 190
Phe Gly Tyr Arg Gly Val Ser Ser Gln Glu Tyr His Asn Ser Leu Gly
        195                 200                 205
Glu Arg Pro
    210
```

<210> SEQ ID NO 11
<211> LENGTH: 498
<212> TYPE: DNA
<213> ORGANISM: Mus musculus

<400> SEQUENCE: 11

```
atggttcgtc tgcctctgca gtgcgtcctc tggggctgct tgctgaccgc tgtccatcca        60
gaaccaccca ctgcatgcag agaaaaacag tacctaataa acagtcagtg ctgttctttg       120
tgccagccag gacagaaact ggtgagtgac tgcacagagt tcactgaaac ggaatgcctt       180
ccttgcggtg aaagcgaatt cctagacacc tggaacagag agacacactg ccaccagcac       240
aaatactgcg accccaacct agggcttcgg gtccagcaga agggcacctc agaaacagac       300
accatctgca cctgtgaaga aggctggcac tgtacgagtg aggcctgtga gagctgtgtc       360
ctgcaccgct catgctcgcc cggctttggg gtcaagcaga ttgctgtgag accaaagacc       420
tggttgtgca caggcaggc acaaacaaga ctgatgttgt ctgtggtgag tcctggacaa       480
tgggccctgg agaaagcc                                                    498
```

<210> SEQ ID NO 12
<211> LENGTH: 166
<212> TYPE: PRT
<213> ORGANISM: Mus musculus

<400> SEQUENCE: 12

```
Met Val Arg Leu Pro Leu Gln Cys Val Leu Trp Gly Cys Leu Leu Thr
1               5                   10                  15
Ala Val His Pro Glu Pro Pro Thr Ala Cys Arg Glu Lys Gln Tyr Leu
                20                  25                  30
Ile Asn Ser Gln Cys Cys Ser Leu Cys Gln Pro Gly Gln Lys Leu Val
            35                  40                  45
Ser Asp Cys Thr Glu Phe Thr Glu Thr Glu Cys Leu Pro Cys Gly Glu
    50                  55                  60
Ser Glu Phe Leu Asp Thr Trp Asn Arg Glu Thr His Cys His Gln His
65                  70                  75                  80
Lys Tyr Cys Asp Pro Asn Leu Gly Leu Arg Val Gln Gln Lys Gly Thr
                85                  90                  95
Ser Glu Thr Asp Thr Ile Cys Thr Cys Glu Glu Gly Trp His Cys Thr
            100                 105                 110
Ser Glu Ala Cys Glu Ser Cys Val Leu His Arg Ser Cys Ser Pro Gly
        115                 120                 125
Phe Gly Val Lys Gln Ile Ala Val Arg Pro Lys Thr Trp Leu Cys Asn
    130                 135                 140
```

```
-continued

Arg Gln Ala Gln Thr Arg Leu Met Leu Ser Val Val Ser Pro Gly Gln
145                 150                 155                 160

Trp Ala Leu Glu Lys Ala
                165
```

US 8,324,165 B2

COMPOSITIONS FOR TREATING ARTHRITIS COMPRISING HG1023575 POLYPEPTIDE

TECHNICAL FIELD

This application generally relates to compositions and methods for treating arthritis and/or other diseases involving cartilage degeneration by delivering one or more therapeutic agents to a subject.

Throughout this application various publications are referenced. The disclosures of these publications in their entireties are hereby incorporated by reference into this application in order to more fully describe the state of the art to which this invention pertains.

BACKGROUND ART

Arthritis has a serious impact on people's lives. Eleven point three percent (23.2 million) of Americans—more people than the population of Texas—report symptoms of arthritis. Among the many different kinds of arthritis conditions, osteoarthritis is the most common afflicting over 20 million people in the United States.

Osteoarthritis is a disease of the whole joint in which most or all articular structures are affected. Its etiology is largely unknown, but is most likely multi-factorial. Osteoarthritis poses a dilemma: it often begins attacking different joint tissues long before middle age, but cannot be diagnosed until it becomes symptomatic decades later, at which point structural alterations are already quite advanced.

In normal joints, a firm, visco-elastic tissue namely, cartilage, covers the ends of each bone. Cartilage acts as a smooth, gliding structure and as a cushion between the bones there by preventing biomechanical damage caused by severe loading. It is mainly composed of collagen and proteoglycan and sole cellular components, the chondrocytes. Chondrocytes comprise the single cellular component of adult hyaline cartilage and are considered to be terminally differentiated cells that maintain the cartilage matrix under normal conditions of low turnover. The dense network of aggrecan (aggregating chondroitin sulphate proteoglycan) and collagen fibers is essential for the biomechanical properties of the cartilage.

Aside from reducing one's weight and avoiding activities that exert excessive stress on the joint cartilage, there is no specific treatment to halt cartilage degeneration or to repair damaged cartilage in arthritis including osteoarthritis. Currently, the goal of treatment in osteoarthritis is merely palliative and is thus limited. Treatment merely involves reducing joint pain and inflammation while improving and maintaining joint function. There thus remains a need for alternative treatment options for osteoarthritis.

BRIEF DESCRIPTION OF THE FIGURES

FIG. 1A shows the chondrocytes during primary culture (P0). FIG. 1B shows the chondrocytes after one passage (P1). FIG. 1C shows the chondrocytes after 4 passages (P4).

FIG. 6 shows a representative result of a high throughput screening of proteins from a protein library in a proteoglycan synthesis assay.

BRIEF DESCRIPTION OF THE TABLES

Figure 1:
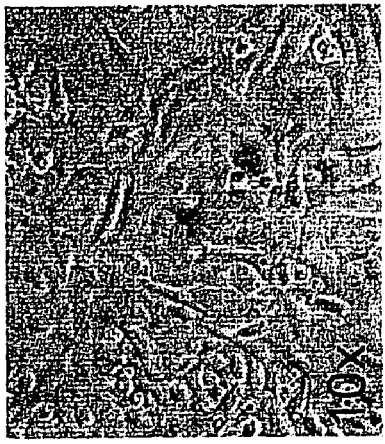
FIG. 1 shows photomicrographs of chondrocytes at different stages of preparation after isolation from articular cartilage.
Figure 1:
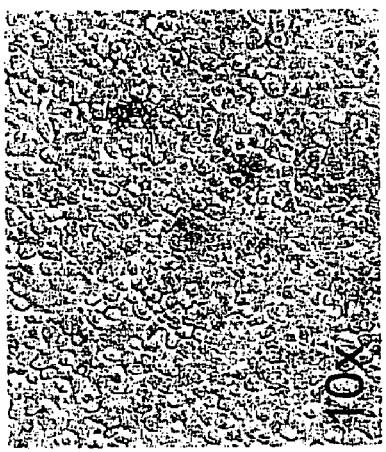
Figure 1:
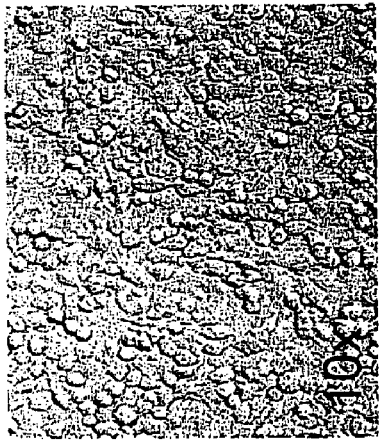

Table 1 provides a list of novel anabolic hits from the high throughput screening of test proteins in a proteoglycan synthesis assay as described in Example 9. Test proteins that yielded significant anabolic activity (probability value equal or less than 0.007), using a rank sum analysis calculated in accordance to the method in Example 9, were each designated as an "anabolic hit."

Table 2 shows the SEQ ID NOs. of the novel anabolic hits and their nucleic acid sequences (N1 sequences).

Table 3 provides the amino acid sequences (P1 sequences) encoded by the corresponding nucleic acid sequences of Table 2. The N1 and P1 sequences are correlated as shown in Table 1.

INDUSTRIAL APPLICABILITY

The compositions and methods and kits of the invention are useful in the treatment of arthritis and/or diseases involving cartilage degeneration or deficiency. They are also useful in promoting cell survival, differentiation, proliferation, and regeneration.

SUMMARY OF THE INVENTION

The molecules of the present invention and their uses were discovered from a proteoglycan synthesis assay for identifying factors or candidate agents that affect cartilage repair and/or generation. Cartilage contains chondrocytes and proteoglycan. Certain growth factors or other polypeptides may help to promote cartilage regeneration both in vitro and in vivo. A proteoglycan synthesis assay can identify such polypeptides and can be used to assess the effect of growth factors or other factors on cartilage repair and/or generation (for example, see Example 5, below).

The present invention thus provides novel polypeptides that can be used for repair and/or synthesis of cartilage, and/or for treatment of arthritis in subjects in which such repair, synthesis and/or treatment is desirable. In addition, the present invention provides for the corresponding polynucleotides, cells containing such polynucleotides, modulators of such polypeptides and polynucleotides, and for pharmaceutical compositions comprising the foregoing. Exemplary embodiments of the present invention are set forth as follows.

The invention provides isolated polypeptides comprising a polypeptide with an amino acid sequence that is at least 95% identical to the amino acid sequence of SEQ ID NOs:2, 4, 6, 8, 10 and/or 12. In certain embodiments, the present invention provides isolated polypeptides comprising the amino acid sequence of SEQ ID NO:2. In certain embodiments, the present invention provides isolated polypeptides consisting of the amino acid sequence of SEQ ID NOs:2, 4, 6, 8, 10 and/or 12. The invention also includes active fragments of the foregoing polypeptides.

In certain embodiments, the invention provides isolated polynucleotides comprising a polynucleotide which is at least 95% identical to a polynucleotide encoding a polypeptide having the amino acid sequence set forth in SEQ ID NOs:2, 4, 6, 8, 10 and/or 12 which promotes proteoglycan production. In certain embodiments, the invention provides isolated polynucleotides comprising a polynucleotide which is at least 95% identical to a polynucleotide having the nucleic acid sequence set forth in SEQ ID NOs:1, 3, 5, 7, 9 or 11 which promotes proteoglycan production. In certain embodiments, the invention provides isolated polynucleotides encoding a polypeptide having the amino acid sequence set forth in SEQ ID NOs:2, 4, 6, 8, 10 and/or 12. The invention also includes active fragments of the foregoing polynucleotides.

In certain embodiments, the invention provides pharmaceutical compositions for treating arthritis in a subject comprising at least a first therapeutic agent and a pharmaceutically acceptable carrier, wherein the first therapeutic agent comprises a polypeptide with an amino acid sequence that is at least 95% identical to SEQ ID NOs:2, 4, 6, 8, 10 and/or 12.

The pharmaceutical compositions of any of the above may be adapted to be administered locally or systemically. In addition, the pharmaceutical compositions of any of the above may adapted to be administered subcutaneously, intramuscularly, intra-articularly, transdermally, by inhalation, intranasally, orally, intraperitoneally or intravenously.

The pharmaceutically acceptable carrier of any of the above pharmaceutical compositions may comprise a biodegradable carrier. In certain embodiments, the biodegradable carrier comprises a polysaccharide. In certain of those embodiments, the polysaccharide may comprise hyaluronic acid, dextran, dextran sulfate, chondroitin sulfate, dennatan sulfate, keratan sulfate, heparin, heparin sulfate, and/or alginate. The pharmaceutically acceptable carrier of any of the above pharmaceutical compositions may comprise a polymer of polylactic acid and polyglycolic acid.

The pharmaceutical compositions of any of the above may further comprise a second therapeutic agent. The second therapeutic agent may comprise a second anabolic factor, which may comprise any of the anabolic factors of the present invention. In certain embodiments, the second therapeutic agent comprises an inhibitory agent. The inhibitory agent may comprise an anti-inflammatory agent. In certain embodiments, the inhibitory agent comprises an anti-catabolic agent that inhibits degradation of proteoglycan or that inhibits apoptosis of chondrocytes. In certain embodiments, the inhibitory agent comprises an inhibitor of the polypeptide of SEQ ID NOs:2, 4, 6, 8, 10 and/or 12. In certain embodiments, the inhibitory agent comprises an antibody. The antibody may be a monoclonal antibody.

In any of the pharmaceutical compositions of the above, the therapeutic factor may further comprise a fusion partner. In certain embodiments, the fusion partner may comprise a polymer, an immunoglobulin molecule, a succinyl group, fetuin A, fetuin B, albumin, a leucine zipper domain, an oligomerization domain, a mannose binding protein, a macrophage scavenger protein, or an active fragment of any of these. In certain of those embodiments, the dimerization domain comprises an Fc fragment of an immunoglobulin. The immunoglobulin may be an IgG or an IgM molecule. In certain embodiments, the polypeptide is pegylated. The invention also provides polynucleotides encoding the above fusion proteins.

The pharmaceutical compositions of the invention may further comprise one or more NSAIDS selected from the group consisting of acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol. The pharmaceutical compositions of the invention may also further comprise one or more DMARDS selected from the group consisting of dihydrofolic acid reductase inhibitors e.g., methotrexate; cyclophosphamide; cyclosporine; cyclosporin A; chloroquine; hydroxychloroquine; sulfasalazine (sulphasalazopyrine) gold salts D-penicillamine; leflunomide; azathioprine; anakinra; and TNF blockers e.g., infliximab (REMICADE®) or etanercept. In certain embodiments, the dihydrofolic acid reductase inhibitor is methotrexate. In certain embodiments, the TNF blocker is any one of infliximab (REMICADE®) and etanercept.

The invention provides vectors comprising one or more nucleic acid molecules of the invention and a regulatory sequence that regulates the expression of the nucleic acid molecule. The invention also provides recombinant host cell comprising a cell and one or more nucleic acid molecules of the invention. The recombinant host cell may be an embryonic stem cell, an adult stem cell, a mesenchymal stem cell, a bone marrow stem cell, a progenitor cell, or a chondrocyte.

The invention also provides methods for treating arthritis by inducing cartilage synthesis and/or repair in a subject comprising administering the above pharmaceutical compositions. In certain embodiments, the cartilage synthesis and/or repair is induced in a spinal disc or in a joint of an animal subject. In certain embodiments, the arthritis treated by the methods of the invention is rheumatoid arthritis, osteoarthritis, lupus-associated arthritis, or psoriatic arthritis. The invention also provides methods for treating a proteoglycan deficiency in a subject comprising providing the above polypeptides or pharmaceutical compositions to the subject. The subject may be a human.

The invention further provides methods of promoting cartilage synthesis and/or repair subject comprising providing a composition comprising recombinant host cells of the invention; and administering the composition to the subject.

The pharmaceutical compositions of the invention may be administered locally or systemically. In certain embodiments, the pharmaceutical composition is administered subcutaneously, intramuscularly, intra-articularly, transdermally, by inhalation, intranasally, orally, intraperitoneally or intravenously.

DETAILED DESCRIPTION OF THE INVENTION

Definitions

An "anabolic factor" is a protein or polypeptide, or the polynucleotide that encodes such, that promotes proteoglycan synthesis and/or collagen synthesis and thereby promotes cartilage synthesis, repair and/or generation. Anabolic factor includes "anabolic hits" of the invention as shown in Table 1.

The term "stimulates proteoglycan synthesis" means causing increased proteoglycan production by chondrocytes. For example, this can be evidenced in assays, as demonstrated by increased levels of incorporation of radiolabel in proteoglycan molecules present either in culture extracellular matrix or in culture supernatants.

The term "arthritis" includes, but is not limited to, osteoarthritis, rheumatoid arthritis, lupus-associated arthritis, juvenile idiopathic arthritis, reactive arthritis, enteropathic arthritis and psoriatic arthritis.

The term "diseases involving cartilage degeneration" is any disease or disorder involving cartilage and/or joint degeneration. The term "diseases involving cartilage degeneration" includes disorders, syndromes, diseases, and injuries that affect spinal discs or joints in animals, including humans, e.g., articular joints, and include, but are not limited to, chondrophasia, spondyloarthropathy, ankylosing spondylitis, lupus erythematosus, relapsing polychondritis, and Sjogren's syndrome.

A "proteoglycan synthesis assay" is a method of determining levels of synthesis of proteoglycans by cells. This can be conducted, for example, by adding into the cell culture, for a set period of time, a labeled precursor, such as a radiolabelled precursor, that can be incorporated into new proteoglycan molecules as they are synthesized in the cells. Proteoglycans can then be separated from other molecules in the cultures, and the amount of incorporated radiolabel can be measured, which correlates with the amount of proteoglycan molecules synthesized during the time period tested.

A "growth factor" is a hormone or a polypeptide that stimulates a cell to grow, proliferate or differentiate. Many types and families of growth factors exist, including protein hormones and steroid hormones.

"DMARDs" refer to a Disease Modifying Anti-Rheumatic Drug and can include, but are not limited to, dihydrofolic acid reductase inhibitors e.g., methotrexate; cyclophosphamide; cyclosporine; cyclosporin A; chloroquine; hydroxychloroquine; leflunomide; azathioprine; anakinra; and TNF blockers e.g., infliximab (REMICADE®) or etanercept.

"NSAIDs" refer to a Non-Steroidal Anti-Inflammatory Drug and reduce inflammatory reactions in a subject. NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol.

A "gel composition" is a gel comprising a biocompatible polymer which is typically dissolved in a solvent. Viscosity of a gel composition can be adjusted to accommodate desired release kinetics and to sustain or control the release of a therapeutic agent in the gel composition. With the use of a temperature-sensitive polymer, a gel composition can be a liquid before administration to the patient and become a gel within the patient.

A "biodegradable carrier" comprises a composition that can be broken down and absorbed in an animal, such as a human. An example of a biodegradable carrier is polylactic acid and polyglycolic acid homo- or hetero-polymers.

A "biomarker" is a biologically-compatible substance whose presence in a patient or in a patient sample can be visualized or detected by any of a variety of methods, including, but not limited to, ELISA assays, X-rays, computed tomography (CT), magnetic resonance imaging (MRI), molecular imaging, and positron emission tomography (PET).

A "variant" of a protein includes both naturally occurring and artificially produced polypeptide, for example, genetically engineered proteins, that differ from the wild-type protein. Differences from the wild-type protein may include, but are not limited to, single or multiple amino acid substitutions, truncations, deletions, insertions, and repetitions. The amino acid substitutions can be conservative or non-conservative.

A "fusion molecule" is a molecule, for example, a polynucleotide, polypeptide, or other polymer, that contains all or portions of more than one gene linked together as one molecule. For example, a fusion protein can be produced from splicing strands of recombinant DNA and expressing the hybrid gene. A fusion molecule can be made by genetic engineering, for example, by removing the stop codon from the DNA sequence of the first protein, then appending the DNA sequence of the second protein in-frame. That DNA sequence will then be expressed by a cell as a single protein. Typically this is accomplished by cloning a cDNA into an expression vector in frame with an existing gene.

A "fusion partner" is a molecule that is linked to a polypeptide or polynucleotide, such as one having therapeutic or prophylactic value. A fusion partner can also be a polynucleotide, or polypeptide, or other polymer. For example, a polypeptide can be fused in-frame at the N-terminus and/or C-terminus of, or internally to, a therapeutic or prophylactic polypeptide. For example, the fusion partner may be albumin, any variant of albumin, or any fragment thereof. Another fusion partner may be any variant of fetuin, or any fragment thereof. Yet another fusion partner may be the Fc domain of an immunoglobulin or a variant thereof. See, e.g., U.S. Pat. Nos. 5,116,964; 5,225,538; 5,428,130; 5,455,165; 5,514,582; 5,714,147; and 6,406,697.

The terms "agent," "substance," "modulator," and "compound" are used interchangeably herein. These terms refer to a substance that binds to and/or modulates a level or activity of a polypeptide, or a level of mRNA encoding a polypeptide, or nucleic acid, or that modulates the activity of a cell containing a polypeptide or nucleic acid. These terms also encompass an active substance that can be used to treat arthritis and/or diseases involving cartilage degeneration (such as osteoarthritis, rheumatoid arthritis, lupus-associated arthritis and psoriatic arthritis). Where the agent modulates a level of mRNA encoding a polypeptide, agents include ribozymes, antisense, and RNAi molecules. Where the agent is a substance that modulates a level of activity of a polypeptide, agents include antibodies specific for the polypeptide, peptide aptamers, small molecule drugs, agents that bind a ligand-binding site in the polypeptide, natural ligands, soluble receptors, agonists, antagonists, and the like. Antibody agents include antibodies that specifically bind a subject polypeptide and activate the polypeptide, such as receptor-ligand binding that initiates signal transduction; antibodies that specifically bind a subject polypeptide and inhibit binding of another molecule to the polypeptide, thus preventing activation of a signal transduction pathway; antibodies that bind a subject polypeptide to modulate transcription; antibodies that bind a subject polypeptide to modulate translation; as well as antibodies that bind a subject polypeptide on the surface of a cell to initiate antibody-dependent cytotoxicity (ADCC) or to initiate cell killing or cell growth. Small molecule drug modulators also include those that bind the polypeptide to modulate activity of the polypeptide or a cell containing the polypeptide. Where the agent modulates the activity of a cell, the agent includes surgery, radiation therapy, chemotherapy or a biologically actively molecule.

A "therapeutic agent" refers to an agent or modality that is useful for treatment of a disease, including any one or more of a biologically active molecule such as one having an agonistic effect in promoting treatment of disease or an anti-antagonistic effect in inhibiting disease progression, and comprises any one or more of the anabolic factors of Tables 1-3.

A "long-acting therapeutic agent" refers to a therapeutic agent modified to have a longer in vivo half-life than the agent in the absence of the modification.

A "disease" refers to any deficiency, defect, pathology or abnormality in any bodily organs, tissues, cells, functions, bodily parts or activity in a subject, such as a human, and includes any disease, disorder, syndrome, and condition "Treat," "Treating" or "Treatment," as used herein, covers any administration or application of remedies for disease in a mammal, including a human, and includes inhibiting the disease, arresting its development, preventing its progression, or relieving the symptoms, or ameliorating the effects of the disease for example, by causing regression, or restoring or repairing a lost, missing, or defective function; or stimulating an inefficient or absent process.

"Prophylaxis," as used herein, includes preventing a disease from occurring or recurring in a subject that may be predisposed to the disease but is not currently symptomatic. Treatment and prophylaxis can be administered to an organism, or to a cell in vivo, in vitro, or ex vivo, and the cell subsequently administered to the subject.

A "therapeutically effective amount" refers to a dose of a therapeutic agent capable of treating a particular condition or disease, for example, arthritis and/or diseases involving cartilage degeneration. A therapeutically effective amount may be effective upon the first administration or it may require more than one administration to achieve a desired therapeutic effect.

"Half-life" is the time needed for the concentration of a foreign substance in a body fluid to decrease to half of its original value.

An "Fc molecule" refers to that part of a heavy chain of an immunoglobulin molecule that does not bind to a light chain and does not contain an antigen binding site. It may be in a monomeric or a dimeric form and may be fused to another molecule, such as one of the anabolic hits herein, facilitating the formation of a dimerized fusion molecule.

An "antibody CH3 domain" refers to the C-terminal immunoglobulin domain of a heavy chain of an immunoglobulin molecule. Folding and assembly of the non-covalent homodimer formed by antibody CH3 domains have been studied. See Thies et al., J. Mol. Biol. (1999) 293:67-79.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. Suitable carriers include, but are not limited to, water, dextrose, glycerol, saline, ethanol, and combinations thereof. The carrier may contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

A "device" for delivery of the compositions of the present invention is any conventional means appropriate for the mode of delivery intended. For example, if the composition is to be injected, the device includes a needle or needleless syringe or a catheter; if the composition is to be delivered transdennally, the device includes a transdennal patch; if the composition is to be implanted, the device includes a biodegradable or non-biodegradable matrix for holding the composition.

"Injection" is the introduction of a substance into the body. Injection may introduce substances into muscular tissue; subcutaneous tissue; a vascular lumen, for example a vein or artery; synovium or articular joint; or other cavities or canals of the body, for example. The term "injection" includes the use of any suitable device to effect the introduction. The term includes, for example, introduction by catheter. The term also includes, for example, the direct injection of a substance to the joint area.

The terms "subject," "host," "individual," "animal," and "patient," used interchangeably herein, refer to mammals, including humans, and also include, but are not limited to, murines, simians, felines, canines, equines, bovines, porcines, ovines, caprines, rabbits, mammalian farm animals, mammalian sport animals, and mammalian pets. In many embodiments, the subjects will be humans. Animal models are of interest for experimental investigations, providing a model for treatment of human disease.

Described herein, are compositions and methods that are useful in treating arthritis and/or diseases involving cartilage degeneration or deficiency. The molecules of the invention were identified by employing several in vitro cell-based assays.

Pharmaceutical Compositions

The present invention provides compositions that are useful in treating arthritis and/or diseases involving cartilage degeneration or deficiency, including pharmaceutical compositions, comprising the novel anabolic polypeptide factors of Table 1 or modulators of such factors.

The compositions may include a buffer, which is selected according to the desired use of the polypeptide, polynucleotide, or other therapeutic agent, and may also include other substances appropriate to the intended use. Those skilled in the art can readily select an appropriate buffer, a wide variety of which are known in the art, suitable for an intended use. The compositions may also include a biodegradable scaffold, matrix or encapsulating material such as liposomes, microspheres, nanospheres and other polymeric substances. In some instances, the composition can comprise a pharmaceutically acceptable carrier or excipient, a variety of which are known in the art and need not be discussed in detail herein. Pharmaceutically acceptable excipients have been amply described in a variety of publications, including, for example, Gennaro, A. R. (2003) Remington: The Science and Practice of Pharmacy with Facts and Comparisons: Drugfacts Plus. $20^{th}$ ed., Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed., Amer. Pharmaceutical Assoc. In some embodiments, the composition comprises a matrix that allows for slow release of the composition.

The pharmaceutically acceptable excipients, such as vehicles, adjuvants, carriers, and diluents, are readily available to the public. Moreover, pharmaceutically acceptable auxiliary substances, such as pH adjusting and buffering agents, tonicity adjusting agents, stabilizers, wetting agents and the like, are readily available to the public.

The therapeutic agents may be obtained from naturally occurring sources or synthetically or recombinantly produced. Where obtained from naturally occurring sources, the source chosen will generally depend on the species from which the protein is to be derived. The subject proteins may also be derived by synthesis, such as by synthesizing small fragments of a polypeptide and later linking the small fragments together. The subject protein can be more efficiently produced by recombinant techniques, such as by expressing a recombinant gene encoding the protein of interest in a suitable host, whether prokaryotic or eukaryotic, and culturing such host under conditions suitable to produce the protein. If a prokaryotic host is selected for production of the protein, such as E. coli, the protein will typically be produced in and purified from the inclusion bodies. If an eukaryotic host is selected for production of the protein, such as CHO or 293 cells, the protein may be secreted into the culture medium when its native or a heterologous secretory leader sequence is linked to the polypeptide to be made. Any convenient protein purification procedures may be employed. Suitable protein purification methodologies are described in Guide to Protein Purification, Deuthser ed. (Academic Press, 1990). For example, a lysate may be prepared from the original source and purified using HPLC, exclusion chromatography, gel electrophoresis, affinity chromatography, and the like.

Therapeutic compositions of the invention may comprise polypeptides, small organic molecules, carbohydrates, and lipids. These may, in appropriate circumstances, take the form of monomers or polymers.

Candidate therapeutic agents for use in the present compositions may be obtained through a screening process using a wide variety of sources including libraries of synthetic or natural compounds in a screening assay. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical, and biochemical means, and may be used to produce combinatorial libraries. Known pharmacological agents may be subjected to directed or random chemical modifications, such as acylation, alkylation, esterification, amidification, etc. to produce structural analogs.

Candidate therapeutic agents may be obtained from a study of changes in gene expression profiles brought about by arthritis or other diseases involving degeneration of cartilage (such as osteoarthritis). Gene expression profiling may be accomplished by a variety of techniques, including, but not limited to, differential display, serial analysis of gene expression (SAGE), subtractive hybridization, and gene microarrays (gene chips). Gene expression microarrays and DNA chips have been discussed in a number of publications, e.g., Hardiman, Pharmacogenomics (2004) 5:487-502. These techniques enable rapid identification of genes whose expression levels are affected by arthritis or other diseases involving degeneration of cartilage (such as osteoarthritis). Such genes and their gene products are candidate agents for treating arthritis or other diseases involving degeneration of cartilage (such as osteoarthritis).

The screening assay of the present invention for identifying candidate agents detects incorporation of a label, where the label can directly or indirectly provide a detectable signal. Various labels may be used, including radioisotopes, fluorescers, chemiluminescers, and the like.

A variety of other reagents may be included in the screening assay. These include reagents like salts, detergents, neutral proteins, e.g. albumin, etc., that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening.

The therapeutic agents can be formulated into preparations for delivery by dissolving, suspending or emulsifying them in an aqueous solvent, such as phosphate buffered saline (PBS), or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be provided in unit dosage forms, i.e., physically discrete units suitable as unitary dosages for human and animal subjects, each unit containing a predetermined quantity of compounds of the present invention (any one or more of a factor of Table 1 or an active fragment thereof) calculated in an amount sufficient to produce the desired effect in association with a pharmaceutically acceptable diluent, carrier, or vehicle. The specifications for the novel unit dosage forms of the present invention depend on the particular compound employed and the effect to be achieved, and the pharmacodynamics associated with each compound in the host.

An effective amount of the therapeutic agent(s) (for example, a subject polypeptide of the invention) is administered to the subject at a dosage sufficient to produce a desired result. For example, the desired result is a decrease in arthritis progression or in the severity of arthritis as compared to a control. A decrease in arthritis progression or severity may be indicated by a variety of indicia known in the art or described herein (for example, an increase in cartilage, proteoglycan and/or collagen synthesis).

Typically, the compositions of the instant invention will contain from less than about 1% to about 95% of the active ingredient, in some embodiments, about 10% to about 50%. Generally, between about 1 microgram (μg) and about 500 mg of the compositions will be administered to a child and between about 5 μg and 5 gram will be administered to an adult either in a single dose or as an accumulative dose over a period of time. Administration is generally by injection and often by injection to a localized area, such as articular joint or adjacent to a spinal disc. The frequency of administration will be determined by the care giver based on patient responsiveness. Other effective dosages can be readily determined by one of ordinary skill in the art through trials establishing dose response curves.

In order to calculate the amount of therapeutic agent to be administered, those skilled in the art could use readily available information with respect to the amount of agent necessary to have the desired effect. The amount of an agent necessary to increase a level of active subject polypeptide can be calculated from in vitro or in vivo experimentation. The amount of agent will, of course, vary depending upon the particular agent used and the condition of the subject being treated, such as the subject's age, the extent of the subject's disease, the subject's weight and the likelihood of any adverse effect, etc.

For example, an effective amount of the therapeutic agent may be an amount of about 0.001 mg/kg to about 100 mg/kg weight of a subject. In another embodiment, the effective amount may be about 0.005 mg/kg to about 50 mg/kg weight of a subject, or about 0.01 mg/kg to about 25 mg/kg weight of a subject, or about 0.05 mg/kg to about 15 mg/kg weight of a subject, or about 0.1 mg/kg to 10 mg/kg weight of a subject, or about 0.5 mg/kg to about 5 mg/kg weight of a subject,or about 1 mg/kg to about 2.5 mg/kg weight of a subject.

Regarding pharmaceutical dosage forms, the therapeutic agents may be administered in the form of their pharmaceutically acceptable salts, or they may also be used alone or in appropriate association, as well as in combination, with other pharmaceutically active compounds or treatment procedures. The following methods and excipients are merely exemplary and are in no way limiting.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Gennaro, A. R. (2003) Remington: The Science and Practice of Pharmacy with Facts and Comparisons: Drugfacts Plus. $20^{th}$ ed., Lippincott, Williams, & Wilkins. The composition or formulation to be administered will, in any event, contain a quantity of the therapeutic agent adequate to achieve the desired state in the subject being treated.

The compositions of the invention will be formulated and dosed in a fashion consistent with good medical practice, taking into account the clinical condition of the individual subject, the site of delivery of the polypeptide composition, the method of administration, the scheduling of administration, and other factors known to practitioners. The effective amount of polypeptide for purposes herein is thus determined by such considerations.

Therapeutic Polynucleotides

The invention covers nucleic acid compositions that encode the therapeutic polypeptides or fragments thereof. Polynucleotides of the invention include those in Table 2 (e.g. SEQ ID NOs:1, 3, 5, 7, 9 and 11) and those encoding the anabolic polypeptides of Table 3, as described herein.

By nucleic acid composition is meant a composition comprising a polynucleotide of DNA or RNA, including one having an open reading frame that encodes a therapeutic polypeptide (e.g., any of the anabolic factors of Tables 1 and/or 3) and is capable, under appropriate conditions, of being expressed as one of the therapeutic polypeptides of the instant invention. However, the term encompasses genomic DNA, cDNA, mRNA, splice variants, antisense RNA, RNAi, DNA comprising one or more single-nucleotide polymorphisms (SNPs), and vectors comprising the subject nucleic acid sequences. Also encompassed in this term are nucleic acids that are homologous or substantially similar or identical to the nucleic acids of Table 1-2 or nucleic acids encoding the therapeutic polypeptides or proteins of Table 1 and/or 3 (that is, the parent proteins or nucleic acid molecules), including ones that are about 99% homologous, or about 98% homologous, or about 97% homologous, or about 96% homologous, or about 95% homologous, or about 90% homologous, or about 85% homologous, or about 80% homologous, or about 75% homologous, or about 70% homologous. Such homologous polynucleotides and polypeptides comprise at least one activity of the parent proteins or nucleic acid molecules. Thus, the subject invention provides genes encoding a subject protein, and homologs thereof.

Polynucleotides or nucleic acids of the invention refer to polymeric forms of nucleotides of any length. The polynucleotides can contain deoxyribonucleotides, ribonucleotides, and/or their analogs or derivatives. For example, nucleic acids can be naturally occurring DNA or RNA, or can be synthetic analogs, as known in the art. Polynucleotides of the invention also encompass genomic DNA, genes, gene fragments, exons, introns, regulatory sequences, or regulatory elements, such as promoters, enhancers, initiation and termination regions, other control regions, expression regulatory factors, and expression controls; DNA comprising one or more single-nucleotide polymorphisms (SNPs), allelic variants, isolated DNA of any sequence, and cDNA; mRNA, tRNA, rRNA, ribozymes, splice variants, antisense RNA, antisense conjugates, RNAi, and isolated RNA of any sequence; recombinant polynucleotides, heterologous polynucleotides, branched polynucleotides, labeled polynucleotides, hybrid DNA/RNA, polynucleotide constructs, vectors comprising the subject nucleic acids, nucleic acid probes, primers, and primer pairs.

Polynucleotides of the invention (for example, those encoding the anabolic factors of Table 1-2 encompass modified nucleic acid molecules, with alterations in the backbone, sugars, or heterocyclic bases, such as methylated nucleic acid molecules, peptide nucleic acids, and nucleic acid molecule analogs, which may be suitable as, for example, probes if they demonstrate superior stability and/or binding affinity under assay conditions. They also encompass single-stranded, double-stranded, and triple helical molecules that are either DNA, RNA, or hybrid DNA/RNA and that may encode a full-length gene or a biologically active fragment thereof.

Polynucleotides of the invention include single nucleotide polymorphisms. Single nucleotide polymorphisms (SNPs) occur frequently in eukaryotic genomes. Nature (2001) 409: 860-921. The nucleotide sequence determined from one individual of a species may differ from other allelic forms present within the population. The present invention encompasses such SNPs.

The subject polynucleotides include those that encode variants of the polypeptides described in the instant specification. Thus, in some embodiments, a subject polynucleotide encodes variant polypeptides that include insertions, deletions, or substitutions compared with the polypeptides described herein. Conservative amino acid substitutions include serine/threonine, valine/leucine/isoleucine, asparagine/histidine/glutamine, glutamic acid/aspartic acid, etc. See, e.g., Gonnet et al. (1992) Science 256:1443-1445.

Nucleic acids encoding the proteins and polypeptides of the subject invention may be cDNA or genomic DNA or a fragment thereof. The term "gene" shall be intended to mean the open reading frame encoding specific proteins and polypeptides of the subject invention, and introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The subject polynucleotides are isolated and obtained in substantial purity, generally as other than an intact chromosome, such as in the form of cDNA. Usually, the DNA will be obtained substantially free of other nucleic acid sequences that do not include a sequence or fragment thereof of the subject genes, generally being at least about 50%, usually at least about 90% pure and are typically "recombinant," i. e,. flanked by one or more nucleotides with which it is not normally associated on a naturally occurring chromosome.

The invention provides plasmids, i.e., small, independently replicating pieces of extrachromosomal cytoplasmic DNA that can be transferred from one organism to another, comprising the therapeutic polynucleotides of the invention. Plasmids can become incorporated into the genome of a host or can remain independent. Artificially constructed plasmids are commonly used as cloning vectors. The invention also provides viral or non-viral vectors, i.e., plasmids that can be used to transfer DNA sequences from one organism to another. Expression vectors can be used to express the therapeutic gene products of the invention and typically comprise restriction sites to provide for the insertion of nucleic acid sequences encoding heterologous protein or RNA molecules.

The subject genes and gene fragments are useful in therapy to treat arthritis or other diseases involving cartilage degeneration. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the subject gene or fragment thereof, and a transcriptional termination region. The transcription cassettes may be introduced into a variety of vectors, e.g., plasmid; retrovirus, e.g., lentivirus; adenovirus; and the like, where the vectors are able to transiently or stably be maintained in the cells, usually for a period of at least about one day, more usually for a period of at least about several days to several weeks.

Specifically, the invention provides compositions and methods for treating arthritis and/or diseases involving cartilage degeneration, in a patient by providing a composition comprising a therapeutic polynucleotide e.g. of Table 1-2, or biologically active fragment thereof, or which encodes any one or more of the anabolic factors of Table 1 and/or 3 and administering the composition to the patient.

Therapeutic Polypeptides

The invention provides polypeptides that are useful in treating arthritis and/or diseases involving cartilage degeneration. Polypeptides of the invention include a polymeric form of amino acids of any length, which can include naturally-occurring or non-naturally occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. They include single chain proteins as well as dimers, trimers or multimers. They also include conjugated proteins, fusion proteins, including, but not limited to, glutathione S-transferase (GST) fusion proteins, fusion proteins with a heterologous amino acid sequence, fusion proteins with heterologous and homologous leader sequences, fusion proteins with or without N-terminal methionine residues, pegylated proteins, and immunologically tagged, or his-tagged proteins. Also included in the polypeptides of the invention are variations of naturally occurring proteins, where such variations are homologous or substantially similar to the naturally occurring protein, as well as corresponding homologs from different species. Variants of polypeptide sequences include insertions, additions, deletions, or substitutions compared with the subject polypeptides. The polypeptides of the invention also include peptide aptamers.

For example, suitable polypeptides for use herein whether alone or in combination with other therapeutic agents include, but are not limited to, the polypeptides shown in SEQ ID NOs: 2, 4, 6, 8, 10, 12, 14, and 16. In accordance with the invention, co-administration can be effected concomitantly or in sequence.

The invention also provides combinations of factors (e.g., any of the factors of Table 1) that have synergistic effects. In accordance with the invention, co-administration can be effected concomitantly or in sequence.

Multiple pathways operate in concert to enable chondrocytes to adapt to oxidative stress. Similarly, complex and multi-step pathways govern differentiation and proliferation of chondrocytes. Proteins, polypeptides, enzymes, substrates, transcription factors, and variants thereof involved in these pathways can be used to treat arthritis and/or diseases involving cartilage degeneration in a patient by ensuring that pathways for cartilage survival, growth, proliferation, and differentiation operate as needed. Variants that can be used in the invention include constitutively active forms and activated forms.

Additional variants that can be used in the invention include biotinylated forms, e.g., biotinylated protein or polypeptide in conjunction with streptavidin and biotinylated self-assembling peptide nanofibers (Davis et al., "Targeted delivery of IGF-1 with biotinylated self-assembling peptide nanofibers," presented at the Keystone Symposium on Molecular Biology of Cardiac Diseases and Regeneration (D2), Steamboat Springs, Colo., USA, Apr. 3-8, 2005), and truncated fours.

The therapeutic methods of the invention can modulate physiologic and pathologic processes. This modulation can encompass an increase or a decrease, a stimulation, inhibition, or blockage in the measured activity when compared to a suitable control. Modulation of expression levels includes increasing the level and decreasing the level of an mRNA or polypeptide of interest encoded by a polynucleotide of the invention when compared to a control lacking the agent being tested. In some embodiments, agents of particular interest are those which inhibit a biological activity of a subject polypeptide, and/or which reduce a level of a subject polypeptide in a cell, and/or which reduce a level of a subject mRNA in a cell, and/or which reduce the release of a subject polypeptide from a eukaryotic cell, and/or which reduce the symptoms (e.g., cell death and damage) associated with a medical condition. In other embodiments, agents of interest are those that increase polypeptide activity. Modulating a level of an active subject polypeptide can include increasing or decreasing the activity of a subject polypeptide; increasing or decreasing a level of active polypeptide; and increasing or decreasing a level of mRNA encoding active subject polypeptide. In some embodiments, an agent is a subject polypeptide, where the subject polypeptide itself is administered to an individual.

Specifically, the invention provides compositions and methods for treating arthritis and/or diseases involving cartilage degeneration, in a patient by providing a composition comprising a therapeutic polypeptide of SEQ ID NOs: 2, 4, 6, 8, 10, 12, 14, and 16, or biologically active fragment thereof; and administering the composition to the patient.

Variant and Mutant Polypeptides

It is to be understood that the therapeutic polypeptides covered by the instant invention include biologically active fragments and analogs of therapeutic polypeptides specifically identified, such as the factors mentioned above. Thus, for example, a reference to a polypeptide encompasses not only the full-length polypeptide, but also biologically active fragments and analogs of the polypeptide. A biologically active fragment or analog is capable of treating arthritis and/or diseases involving cartilage degeneration. Analogs of a particular therapeutic polypeptide can differ from the therapeutic polypeptide by amino acid sequence differences, or by modifications (e.g., post-translational modifications), which do not affect sequence, or by both. Analogs of the invention will generally exhibit at least 80%, at least 85%, at least 90%, at least 95%, at least 96%, at least 97%, at least 98% or at least 99% amino acid identity with all or part of the amino acid sequence of a therapeutic polypeptide. Methods for assaying the capacity of biologically active fragments and analogs to treat arthritis and/or diseases involving cartilage degeneration are known in the art, e.g., those described herein.

Protein engineering may be employed to improve or alter the characteristics of the therapeutic polypeptides of the invention. Recombinant DNA technology known to those skilled in the art can be used to create novel mutant proteins or "muteins" including single or multiple amino acid substitutions, deletions, additions, or fusion proteins. Such modified polypeptides can show desirable properties, such as enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., J. Biol. Chem. (1993) 268:2984-2988, reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature from of the protein generally will be retained when less than the majority of the residues of the complete or mature protein are removed from the N-terminus. Whether a particular polypeptide lacking N-terminal residues of a complete protein retains such immunologic activities can be determined by routine methods described herein and otherwise known in the art. Accordingly, the present invention further provides polypeptides having one or more residues deleted from the amino terminus of the amino acid sequences of the molecules shown in Table 1.

Similarly, many examples of biologically functional C-terminal deletion muteins are known. For instance, interferon gamma increases in activity as much as ten fold when 8-10 amino acid residues are deleted from the carboxy terminus of the protein, see, for example, Dobeli et al., J. Biotechnology (1988) 7:199-216.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can be determined by routine methods described herein and otherwise known in the art.

Other Mutants

In addition to terminal deletion forms of the protein discussed above, it also will be recognized by one of ordinary skill in the art that some amino acid sequences of the therapeutic polypeptides of the invention can be varied without significant effect of the structure or function of the protein. If such differences in sequence are contemplated, it should be remembered that there will be critical areas on the protein which determine activity.

Thus, the invention further includes variations of the therapeutic polypeptides of the invention which show substantial biological activity. Such mutants include deletions, insertions, inversions, repeats, and type substitutions, selected according to general rules known in the art, so as have little effect on activity. For example, guidance concerning how to make phenotypically silent amino acid substitutions is provided in Bowie et al., Science (1990) 247:1306-1310, wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections, or screens, to identify sequences that maintain functionality.

These studies report that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, et al., supra, and the references cited therein. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, and replacements between the aromatic residues Phe and Tyr.

Thus, a fragment, derivative, or analog of a polypeptide of Table 1 or 3 or polypeptide encoded by a nucleic acid sequence of Table 1-2 may be (i) one in which one or more of the amino acid residues are substituted with a conserved or non-conserved amino acid residue; such a substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide, a leader or secretory sequence, a sequence employed to purify the above form of the polypeptide, or a proprotein sequence. Such fragments, derivatives, and analogs are deemed to be within the scope of those skilled in the art from the teachings herein.

Thus, the therapeutic polypeptides of the invention may include one or more amino acid substitutions, deletions, or additions, either from natural mutations or human manipulation. As indicated, these changes may be of a minor nature, such as conservative amino acid substitutions, that do not significantly affect the folding or activity of the protein. Conservative amino acid substitutions include the aromatic substitutions Phe, Trp, and Tyr; the hydrophobic substitutions Leu, Iso, and Val; the polar substitutions Glu and Asp; the basic substitutions Arg, Lys, and His; the acidic substitutions Asp and Glu; and the small amino acid substations Ala, Ser, Thr, Met, and Gly.

Amino acids essential for the functions of the therapeutic polypeptides of the invention can be identified by methods known in the art, such as site-directed mutagenesis or alanine-scanning mutagenesis, see, for example, Cunningham and Wells, Science (1989) 244:1081-1085. The latter procedure introduces single alanine mutations. The resulting mutant molecules are then tested for biological activity such as receptor binding, or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because, for example, aggregates can be immunogenic, Pinckard et al., Clin. Exp. Immunol. (1967) 2:331-340; Robbins et al., Diabetes (1987) 36:838-845; Cleland et al., Crit. Rev. Therapeutic Drug Carrier Systems (1993) 10:307-377.

Replacing amino acids can also change the selectivity of the binding of a ligand to cell surface receptors. For example, Ostade et al., Nature (1993) 361:266-268 describes mutations resulting in selective binding of TNF-a to only one of the two known types of TNF receptors. Sites that are critical for ligand-receptor binding can also be determined by structural analysis such as crystallization, nuclear magnetic resonance, or photoaffinity labeling, for example, Smith et al., J. Mol. Biol. (1992) 224:899-904 and de Vos et al., Science (1992) 255:306-312.

The locations and disulfide bonding properties of the growth factors of the invention are known by those of skill in the art. In an embodiment, the invention provides compositions comprising mutant growth factor molecules with cysteine serine mutated to serine. These constructs may be cloned into any suitable vector, as known in the art. These muteins may provide a composition with improved therapeutic properties.

The therapeutic agent can be administered to the patient through various means, e.g., intravenously and intraperitoneally, and in a variety of formulations, e.g., with or without material that slowly releases the therapeutic agent, with or without matrix material that serves as scaffold, and with or without certain kinds of stem cells. Various materials can be used as matrix material, including, but not limited to, collagen (e.g., rat tail collagen, Roche cat #1 179 179), nanofiber, and alginate. In some embodiments, the therapeutic agent can be administered with or without use of devices such as catheters, and with or without monitoring. The therapeutic agent can be used to treat patients with arthritis and/or diseases involving cartilage degeneration.

Therapeutic Fusion Molecules

As one of skill in the art will appreciate, therapeutic polypeptides of the invention can be combined with or joined to heterologous molecules, for example, polypeptides, resulting in chimeric polypeptide molecules. These fusion molecules may facilitate purification. They provide an increased half-life in vivo. This increase has been reported, for example, in chimeric proteins consisting of the first two domains of the human CD4-polypeptide and various domains of the constant regions of the heavy or light chains of mammalian immunoglobulins, for example, EP 0 394 827; Traunecker et al., Nature (1988) 331:84-86. Fusion proteins with a disulfide-linked dimeric structure due to an immunoglobulin portion can also be more efficient in binding and neutralizing other molecules than the therapeutic protein or protein fragment alone, for example, as described by Fountoulakis et al., J. Biochem. (1995) 270:3958-3964. Suitable chemical moieties for derivatization of a heterologous polypeptide include, for example, polymers, such as water soluble polymers, succinyl groups, the constant domain of immunoglobulins, all or part of human serum albumin; fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179, and U.S. Application Nos. 60/589,788 and 60/654,229. Methods of making fusion proteins are well-known to the skilled artisan.

For example, the short plasma half-life of unmodified interferon alpha makes frequent dosing necessary over an extended period of time, in order to treat viral and proliferative disorders. Interferon alpha fused with HSA has a longer half life and requires less frequent dosing than unmodified interferon alpha; the half-life was 18-fold longer and the clearance rate was approximately 140 times slower (Osborn et al., J. Pharmacol. Exp. Ther. (2002) 303:540-548). Interferon beta fused with HSA also has favorable pharmacokinetic properties; its half life was reported to be 36-40 hours, compared to 8 hours for unmodified interferon beta (Sung et al., J. Interferon Cytokine Res. (2003) 23:25-36). A HSA-interleukin-2 fusion protein has been reported to have both a longer half-life and favorable biodistribution compared to unmodified interleukin-2. This fusion protein was observed to target tissues where lymphocytes reside to a greater extent than unmodified interleukin 2, suggesting that it exerts greater efficacy (Yao et al., Cancer Immunol. Immunother. (2004) 53:404-410).

The Fc receptor of human immunoglobulin G subclass 1 has also been used as a fusion partner for a therapeutic molecule. It has been recombinantly linked to two soluble p75 tumor necrosis factor (TNF) receptor molecules. This fusion protein has been reported to have a longer circulating half-life than monomeric soluble receptors, and to inhibit TNFα-induced proinflammatory activity in the joints of patients with rheumatoid arthritis (Goldenberg, Clin. Ther. (1999) 21:75-87). This fusion protein has been used clinically to treat rheumatoid arthritis, juvenile rheumatoid arthritis, psoriatic arthritis, and ankylosing spondylitis (Nanda and Bathon, Expert Opin. Pharmacother. (2004) 5:1175-1186).

Polymers, for example, water soluble polymers, are useful in the present invention as the polypeptide to which each polymer is attached will not precipitate in an aqueous environment, such as typically found in a physiological environment. Polymers employed in the invention will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time, and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone)polyethylene glycol, polypropylene glycol homopolymers (PPG) and other polyakylene oxides, polypropylene oxide/ethylene oxide copolymers, polyoxyethylated polyols (POG) (for example, glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Specifically, a modified heterologous polypeptide of the invention may be prepared by attaching polyaminoacids or branch point amino acids to the polypeptide. For example, the polyaminoacid may be a carrier protein that serves to increase the circulation half life of the polypeptide (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as human serum albumin), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N-terminus, or C-terminus, or other places in between, and also may be connected by a chemical linker moiety to the selected molecule.

Polymers used herein, for example water soluble polymers, may be of any molecular weight and may be branched or unbranched. The polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a modified molecule of the invention.

Polymers employed in the present invention are typically attached to a heterologous polypeptide with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha ($\alpha$) and/or epsilon ($\epsilon$) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a heterologous polypeptide via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a heterologous polypeptide with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (for example, mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified protein. One may select a polymer by molecular weight, branching, etc., the proportion of polymers to protein (polypeptide or peptide) molecules in the reaction mix, the type of reaction to be performed, and the method of obtaining the selected N-terminal chemically modified protein. The method of obtaining the N-terminal chemically modified protein preparation (separating this moiety from other mono-derivatized moieties if necessary) may be by purification of the N-terminal chemically modified protein material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a polymer to the N-terminus of the protein by performing the reaction at a pH which allows one to take advantage of the pKa differences between the $\epsilon$-amino group of the lysine residues and that of the $\alpha$-amino group of the N-terminal residue of the protein. By such selective derivatization, attachment of a polymer to a protein is controlled: the conjugation with the polymer takes place predominantly at the N-terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized polypeptide to include mono- or poly- (for example, 2-4) PEG moieties. Pegylation may be carried out by any of the pegylation reactions known in the art. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art. See, for example, EP 0 401 384; Malik et al., Exp. Hematol. (1992) 20:1028-1035; Francis, Focus on Growth Factors (1992) 3(2):4-10; EP 0 154 316; EP 0 401 384; WO 92/16221; WO 95/34326; and the other publications cited herein that relate to pegylation.

The step of pegylation as described herein may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ε-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a polypeptide of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, Bioconjugate Chem. (1994) 5:133-140. Reaction conditions may be selected from any of those known in the pegylation art or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (for example, >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Additionally, heterologous polypeptides of the present invention and the epitope-bearing fragments thereof described herein can be combined with or joined to parts of the constant domain of immunoglobulins (IgG), resulting in chimeric polypeptides. These particular fusion molecules facilitate purification and show an increased half-life in vivo. This has been shown, for example, in chimeric proteins consisting of the first two domains of the human CD4-polypeptide and various domains of the constant regions of the heavy or light chains of mammalian immunoglobulins, such as EP 0 394 827; Traunecker et al., Nature (1988) 331:84-86. Fusion molecules that have a disulfide-linked dimeric structure due to the IgG part can also be more efficient in binding and neutralizing other molecules than, for example, a monomeric polypeptide or polypeptide fragment alone; see, for example, Fountoulakis et al., J. Biochem. (1995) 270:3958-3964.

In another described embodiment, a human serum albumin fusion molecule may also be prepared as described herein and as further described in U.S. Pat. No. 6,686,179.

Moreover, the polypeptides of the present invention can be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., Proc. Natl. Acad. Sci. (1989) 86:821-824, for instance, hexa-histidine provides for convenient purification of the fusion protein. Another peptide tag useful for purification, the hemagglutinin HA tag, corresponds to an epitope derived from the influenza hemagglutinin protein (Wilson et al., Cell (1984) 37:767-78). Any of these above fusions can be engineered using the polynucleotides or the polypeptides of the present invention.

Delivery of Therapeutic Agents

Further, the present invention provides compositions and methods for treating arthritis and/or other diseases involving cartilage degeneration, by administering to a subject a combination of an effective amount of (1) one or more DMARDs (such as methotrexate or a molecule that blocks TNF interactions, e.g., blocks TNF interactions with its ligand) and (2) an effective amount of any of the factors of the invention, or fragments thereof. In accordance with the invention, co-administration can be effected concomitantly or in sequence.

Effective amounts of the DMARD can range about 0.1 to 40 mg/week. In one embodiment, the effective amount is an amount about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/ week. In one embodiment, an effective amount of a DMARD is an amount about 10 to 30 mg/week.

Additionally, effective amounts of the DMARD can range about 0.1 to 100 mg/week. In one embodiment, the effective amount is ranges about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, about 35 to 40 mg/week, about 40 to 45 mg/week, about 45 to 50 mg/week, about 50 to 55 mg/week, about 55 to 60 mg/week, about 60 to 65 mg/week, about 65 to 70 mg/week, about 70 to 75 mg/week, about 75 to 80 mg/week, about 80 to 85 mg/week, about 85 to 90 mg/week, about 90 to 95 mg/week or about 95 to 100 mg/week.

In another embodiment, the present invention provides compositions and methods for treating arthritis and/or other diseases involving cartilage degeneration, by administering to a subject a combination of an effective amount of (1) one or more NSAIDS and (2) an effective amount of any of the factors of the invention, or fragments thereof. In accordance with the invention, co-administration can be effected concomitantly or in sequence.

Delivery of Therapeutic Agents

Catheterization

A therapeutic composition of the invention can be adapted to be delivered to the joint area by catheter.

The therapeutic agent can be administered locally, e.g., while treating arthritis and/or diseases involving cartilage degeneration, or while performing a diagnostic procedure. The therapeutic agent can also be delivered in anticipation of events that can result in arthritis and/or diseases involving cartilage degeneration. In this regard, the therapeutic agent serves to prevent arthritis and/or diseases involving cartilage degeneration. For example, the therapeutic agent can be delivered a plurality of days prior to surgery. The therapeutic agent can also be useful in providing protection to patients with arthritis and/or diseases involving cartilage degeneration. For these patients, a life-long regimen of the therapeutic agent may be needed.

Direct Injection

Therapeutic compositions have also been delivered to the affected joint area by direct injection into the joint. Direct injection may be performed during surgery. Direct injection may also be performed without surgical access to the affected joint area by injecting the therapeutic composition to the area, guided by the use of an imaging procedure. Any known imaging technique which provides information in real time is suitable for use with the methods disclosed herein of injecting therapeutic compositions of the invention into the affected joint area.

Other Delivery Methods

The therapeutic agent can be delivered in a gel composition. A gel composition provides the advantage of controlled and sustained release of the therapeutic agent over time. A gel composition can comprise a biocompatible polymer and a solvent that dissolves the polymer to form a gel. The gel composition can also contain other substances including surfactants, viscosity controlling agents, complexing agents, antioxidants, other polymers, etc. Viscosity of the gel can be altered, for example, by changing the concentration of the polymer, to accommodate desired release kinetics of the therapeutic agent. Using a temperature-sensitive polymer, the gel composition can be liquid before administration to the patient and become a gel inside the patient. Biocompatible polymers that can be used may be biodegradable and may include, but are not limited to polylactides, polyglycolides, polycaprolactones, polyanhydrides, polyamines, polyurethanes, polyesteramides, polyorthoesters, polydioxanones, poloxamers, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, chitin, chitosan, and copolymers, terpolymers, and mixtures thereof.

Biodegradable carriers can be used to deliver the therapeutic agent. In one embodiment, the carrier comprises a cross-linked first and second polysaccharide, as described by U.S. Pat. No. 6,303,585 B1. The first and second polysaccharides are each a derivative of a member selected from the group consisting of hyaluronic acid, dextran, dextran sulfate, chondroitin sulfate, dermatan sulfate, keratan sulfate, heparin, heparin sulfate, and alginate. Aldehyde groups of the first polysaccharide derived from oxidized sugar rings can form covalent imine crosslinks with the second polysaccharide amine derivative at amine sites. The ratios of the first and second polysaccharides determine both the physical and biological properties of the carrier. For example, the ratio can be manipulated to provide unreacted but active aldehydes for covalent linkage to a therapeutic agent, if desired. Advantages of such cross-linked polysaccharide drug carriers include a prolonged bio-degradation rate, controlled release of the therapeutic agent, and flexibility of formulation in gel-like or sponge-like form to accommodate desired therapeutic intervention. Other carriers that can be used in the instant invention include heparin-alginate polymer and alginate as described in Harada et al., J. Clin. Invest. (1994) 94:623-630 and references cited therein.

To assist in determining the fate and location of the therapeutic agent within the patient, a biomarker can be co-administered with the composition containing the therapeutic agent. In one embodiment, the composition containing the therapeutic agent includes the biomarker. Biomarkers can be visualized or detected by a variety of methods, including, but not limited to, x-rays, computed tomography (CT), magnetic resonance imaging (MRI), molecular imaging, or nuclear medicine techniques such as positron emission tomography (PET). Biomarkers that can be used in the present invention, and methods of making and using them, are known in the art.

The therapeutic agent can be delivered in a matrix composition. The matrix material may serve as scaffold. Various materials can be used as matrix material, including, but not limited to, collagen (for example, rat tail collagen, Roche cat# 1 179 179), nanofiber, and alginate. In some embodiments, the therapeutic agent can be administered with or without use of devices such as catheters, and with or without monitoring.

The therapeutic agent may be delivered once or a plurality of times. The frequency of treatment and amount of therapeutic agent delivered per treatment will depend on a number of variables, including, but not limited to, the extent and nature of the injury; the potency, toxicity, half-life, solubility, and side effects of the therapeutic agent; and the degree of joint function desired. Those of skill will readily appreciate that dose levels can vary as a function of the specific compound, the severity of the symptoms, and the susceptibility of the subject to side effects. A person of ordinary skill in the art, without undue experimentation, will be able to determine the appropriate frequency and amount of therapeutic agent to use for a particular situation. Suitable dosages for a given compound are readily determinable by those of skill in the art by a variety of means. For example, the invention provides any of the anabolic factors of the invention to human subjects. The dose ranges stated herein are based on a 70 kg person and may be adjusted to treat patients of greater or lesser weight. The invention provides any of the anabolic factors of the invention at doses of from about 20 micrograms to about 3 milligrams. The invention provides any of the anabolic factors of the invention at doses of from about 30 micrograms to about 3.5 milligrams. The invention provides any of the anabolic factors of the invention at doses of from about 40 micrograms to about 4 milligrams. The invention provides any of the anabolic factors of the invention at doses of from about 50 micrograms to about 4.5 milligrams. The invention provides any of the anabolic factors of the invention at doses of from about 100 micrograms to about 5 milligrams. The invention provides any of the anabolic factors of the invention at doses of from about 136 micrograms to about 5.5 milligrams. Multiple doses may be provided in one container, such as a vial or a syringe. Thus, the invention provides doses on multiples of those listed above, intended to be provided in multiple doses, for example, two or three doses per container.

The dose may be administered through a variety of routes, including, but not limited to, intravenous, subcutaneous, intramuscular, inhaled, transdermal, etc. Dosing frequency can be once, twice, thrice, once every other month, once every three months, once every six months, once a year, once monthly, once weekly, twice weekly, thrice weekly, every other day, or daily. The dose may be given in one injection, or a plurality of injections, for example, two, three, four, five, six, seven, eight, nine, or ten injections in a given session. The dose may range from 1 nanogram to 10 milligrams.

To determine efficacy of the treatment, various parameters may be monitored using a variety of techniques. For example, magnetic resonance imaging may be used.

The therapeutic agent can be delivered over a period of time by a pump. This delivery may be performed before, simultaneously with, or, or following an acute procedure, such as catheterization, injection, or surgery. The period of time may be in the range of minutes, hours, days, weeks, or months. The pump may be any biocompatible pump, for example, an osmotic pump. The delivery of the agent by a pump may comprise the primary mode of therapy or an adjunctive therapy.

Additional methods that detect or measure DNA damage, cell death, or apoptosis that may be useful in evaluating efficacy of a particular treatment for arthritis and/or diseases involving cartilage degeneration can be employed, for example, in animal studies or on biopsy tissue. DNA damage can be detected using any known method, including, but not limited to, a Comet assay (commercially available from Trevigen, Inc.), which is based on alkaline lysis of labile DNA at sites of damage; and immunological assays using antibodies specific for aberrant DNA structures, for example, 8-OHdG.

Cell death can be measured using any known method, and is generally measured using any of a variety of known methods for measuring cell viability. Such assays are generally based on entry into the cell of a detectable compound (or a compound that becomes detectable upon interacting with, or being acted on by, an intracellular component) that would normally be excluded from a normal, living cell by its intact cell membrane. Such compounds include substrates for intracellular enzymes, including, but not limited to, a fluorescent substrate for esterase; dyes that are excluded from living cells, including, but not limited to, trypan blue; and DNA-binding compounds, including, but not limited to, an ethidium compound such as ethidium bromide and ethidium homodimer, and propidium iodide.

Apoptosis can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) J. Cell Biol. 119:493). The TUNEL method consists of catalytically adding a nucleotide, which has been conjugated to a chromogen system or a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, for example, from Boehringer Mannheim (Cell Death Kit) and Oncor (Apoptag Plus). Another marker that is currently available is annexin, sold under the trademark APOPTEST™. This marker is used in the "Apoptosis Detection Kit," which is also commercially available, for example, from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art.

The therapeutic agent may be delivered alone or in combination with one or more other therapeutic agents. The exact formulation and combination will depend on a number of factors, including, but not limited to, the extent and nature of the injury; mode of action of the therapeutic agents; and any interactions between the therapeutic agents. A person of ordinary skill in the art, without undue experimentation, will be able to determine the appropriate combination for a particular situation.

Antibodies of the Invention

The invention further provides antibodies (e.g., polyclonal, monoclonal, chimeric, and humanized antibodies) that bind to any of the novel proteins of the invention, for example, antibodies that bind to the polypeptides of Table 3, including mutants, variants or fragments of the polypeptide. The most preferred antibodies will selectively bind to any of the novel proteins disclosed herein and will not bind (or will bind weakly) other proteins. The most preferred antibodies will specifically bind to the novel proteins disclosed herein. It is intended that the term "specifically bind" means that the antibody predominantly binds to the novel proteins. Antibodies that are particularly contemplated include monoclonal and polyclonal antibodies as well as fragments thereof (e.g., recombinant proteins) containing the antigen binding domain and/or one or more complement determining regions of these antibodies. These antibodies can be from any source, e.g., rat, dog, cat, pig, horse, mouse or human.

In one embodiment, the antibodies of the invention specifically bind to an active site of the novel proteins. In other embodiments, the antibodies of the invention specifically bind to other domains of the novel proteins, such as a portion of the N-terminal region, the middle region, or the C-terminal region. As will be understood by those skilled in the art, the regions or epitopes of any of the novel proteins to which an antibody is directed may vary with the intended application. For example, antibodies intended for use in an immunoassay for the detection of membrane-bound proteins on viable cells should be directed to an accessible epitope on a membrane-bound novel protein of the invention. Antibodies that recognize other epitopes may be useful for the identification of any of the novel proteins within cells of interest. The invention also encompasses antibody fragments that specifically recognize any of the novel proteins of the invention. As used herein, an antibody fragment is defined as at least a portion of the variable region of the immunoglobulin molecule that binds to its target, i.e., the antigen binding region. Some of the constant region of the immunoglobulin may be included.

In another embodiment, the invention provides various immunological assays useful for the detection of any of the novel protein of the invention. Such assays generally comprise one or more antibodies against any of the novel proteins of the invention, capable of recognizing and binding their target, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. Cancer Research 58: 4055-4060 (1998), immunohistochemical analysis and the like.

Antibodies of the invention may also be used in methods for purifying any of the novel proteins and peptides and for isolating homologues of, and molecules related to the novel proteins of the invention. For example, in one embodiment, the method of purifying any of the novel proteins of the invention comprises incubating the antibody of the invention, which has been coupled to a solid matrix, with a lysate or other solution containing any of the novel proteins, under conditions which permit the antibody of the invention to bind to any of the novel proteins of the invention; washing the solid matrix to eliminate impurities; and eluting the protein from the coupled antibody. Additionally, antibodies of the invention may be used to isolate cells positive for any of the novel proteins of the invention, using cell sorting and purification techniques. Other uses of the antibodies of the invention include generating anti-idiotypic antibodies that mimic any of the novel proteins of the invention, e.g., a monoclonal anti-idiotypic antibody reactive with an idiotype on any of the monoclonal antibodies embodied by the invention.

Various methods for the preparation of antibodies are well known in the art. For example, antibodies may be prepared by immunizing a suitable mammalian host using any of the novel protein of the invention, peptide, or fragment, in isolated or immunoconjugated form (Harlow, Antibodies, Cold Spring Harbor Press, NY (1989)). In addition, fusion proteins of the invention may also be used, such as a any of the novel proteins of the invention fused to, for example a OST-protein. Cells expressing or overexpressing any of the novel proteins of the invention may also be used for immunizations. Similarly, any cell engineered to express any of the novel proteins of the invention may be used. This strategy may result in the production of monoclonal antibodies with enhanced capacities for recognizing endogenous novel proteins of the invention.

Another embodiment of the invention includes chimeric antibodies which are immunoglobulin molecules that comprise a human and non-human portion. The antigen combining region (variable region) of a chimeric antibody can be derived from a non-human source (e.g. murine) and the constant region of the chimeric antibody which confers biological effector function to the immunoglobulin can be derived from a human source. The chimeric antibody should have the antigen binding specificity of the non-human antibody molecule and the effector function conferred by the human antibody molecule.

In general, the procedures used to produce chimeric antibodies can involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;

b) cloning the gene segments encoding the constant region or desired part thereof;

c) ligating the variable region with the constant region so that the complete chimeric antibody is encoded in a form that can be transcribed and translated;

d) ligating this construct into a vector containing a selectable marker and gene control regions such as promoters, enhancers and poly(A) addition signals;

e) amplifying this construct in bacteria;

f) introducing this DNA into eukaryotic cells (transfection) most often mammalian lymphocytes;

g) selecting for cells expressing the selectable marker;

h) screening for cells expressing the desired chimeric antibody; and k) testing the antibody for appropriate binding specificity and effector functions.

Antibodies of several distinct antigen binding specificities have been manipulated by these protocols to produce chimeric proteins (e.g. anti-TNP: Boulianne et al., *Nature* 312: 643 (1984); and anti-tumor antigens: Sahagan et al., *J. Immunol.* 137:1066 (1986)). Likewise, several different effector functions have been achieved by linking new sequences to those encoding the antigen binding region. Some of these include enzymes (Neuberger et al., *Nature* 312:604 (1984)), immunoglobulin constant regions from another species and constant regions of another immunoglobulin chain (Sharon et al., *Nature* 309:364 (1984); Tan et al., *J. Immunol.* 135:3565-3567 (1985)). Additionally, procedures for modifying antibody molecules and for producing chimeric antibody molecules using homologous recombination to target gene modification have been described (Fell et al., *Proc. Natl. Acad. Sci. USA* 86:8507-8511 (1989)).

The amino acid sequence of any of the novel proteins presented herein may be used to select specific regions of the protein for generating antibodies. For example, hydrophobicity and hydrophilicity analyses of the amino acid sequence of any of the novel proteins of the invention may be used to identify hydrophilic regions in the protein structure. Regions of the proteins of the invention that show immunogenic structure, as well as other regions and domains, can readily be identified using various other methods known in the art, such as Chou-Fausman, Garnier-Robson, Kyte-Doolittle, Eisenberg, Karplus-Schultz or Jameson-Wolf analysis. Fragments containing these residues are particularly suited in generating specific classes of antibodies against the novel proteins of the invention.

Methods for preparing a protein for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a immunogen comprising any of the novel proteins of the invention is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is any of the novel proteins of the invention or fragment thereof When the appropriate immortalized cell culture secreting the desired antibody is identified, the cells can be cultured either in vitro or by production in ascites fluid.

The desired monoclonal antibodies may then be recovered from the culture supernatant or from the ascites supernatant. Fragments of the monoclonal antibodies of the invention or the polyclonal antisera (e.g., Fab, F(ab')$_2$, Fv fragments, fusion proteins) which contain the immunologically significant portion (i.e., portion that recognizes and binds any of the novel proteins of the invention) may be used as well as the intact antibodies. Humanized antibodies directed against any of the novel proteins of the invention are also useful. As used herein, a humanized antibody that recognizes and binds any of the novel proteins of the invention is an immunoglobulin molecule which is capable of binding to the proteins of the invention and which comprises a FR region having substantially the amino acid sequence of a human immunoglobulin and a CDR having substantially the amino acid sequence of non-human immunoglobulin or a sequence engineered to bind any of the novel proteins of the invention. Methods for humanizing murine and other non-human antibodies by substituting one or more of the non-human antibody CDRs for corresponding human antibody sequences are well known (see for example, Jones et al., 1986, Nature 321: 522-525; Riechmnan et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Use of immunologically reactive fragments, such as the Fab, Fab', or F(ab')$_2$ fragments maybe preferable, as these fragments are generally less immunogenic than the whole immunoglobulin. Further, bi-specific antibodies specific for two or more epitopes may be generated using methods generally known in the art. Further, antibody effector functions may be modified so as to enhance the effect of antibodies of the invention. For example, cysteine residues may be engineered into the Fc region, permitting the formation of interchain disulfide bonds and the generation of homodimers which may have enhanced capacities for internalization, ADCC and/or complement-mediated cell killing (see, for example, Caron et al., 1992, J. Exp. Med. 176: 1191-1195; Shopes, 1992, J. Immunol. 148: 2918-2922). Homodimeric antibodies may also be generated by cross-linking techniques known in the art (e.g., Wolff et al., Cancer Res. 53: 2560-2565). In an embodiment, the invention provides pharmaceutical compositions having the monoclonal antibodies or anti-idiotypic monoclonal antibodies of the invention.

Alternatively, methods for producing fully human monoclonal antibodies, include phage display and transgenic methods, are known and may be used for the generation of human mAbs (for review, see Vaughan et al., 1998, Nature Biotechnology 16: 535-539). For example, fully human monoclonal antibodies of the invention may be generated using cloning technologies employing large human Ig gene combinatorial libraries (i.e., phage display) (Griffiths and Hoogenboom), building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human monoclonal antibodies of the invention may also be produced using transgenic mice engineered to contain human immunoglobulin gene loci (Jakobovits, 1998, Exp. Opin. Invest. Drugs 7(4): 607-614). This method avoids the in vitro manipulation required with phage display technology and efficiently produces high affinity authentic human antibodies.

The antibody or fragment thereof of the invention may be labeled with a detectable marker or conjugated to a second molecule, such as a diagnostic agent thereby resulting in an immunoconjugate. For example, the agent includes, but is not limited to, a radioactive agent, a second antibody or an enzyme. Further, the invention provides an embodiment wherein the antibody is linked to an enzyme that converts a prodrug into an active form. The immunoconjugate may be used for targeting a second molecule to a cell positive for any of the novel proteins of the invention (Vitetta, E. S. et al., 1993, Immunotoxin therapy, in DeVita, Jr., V. T. et al., eds, Cancer: Principles and Practice of Oncology, 4th ed., J.B. Lippincott Co., Philadelphia, 2624-2636).

Techniques for conjugating or joining agents to antibodies are well known (see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

Dosage Forms

Dosage forms can be made according to well known methods in the art. Some preferred methods are described below.

The pharmaceutical compositions of the invention may be formulated as solid dosage forms, such as capsules, pills, softgels, tablets, caplets, troches, wafer, sprinkle, chewing gum or the like, for oral administration. The pharmaceutical compositions of the invention may also be formulated as liquid dosage forms such as elixir, suspension or syrup.

The pharmaceutical compositions of the invention may also be presented in a dosage form for transdermal application, for example an ointment for children, a form for oral administration, for example a slow release product, or in gastro-resistant tablet form or gum form. They may also be in spray, bronchial form or eye lotion form, or other galenic forms with programmed mucosal and secondarily per os disintegration.

Therefore, the different pharmaceutical compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms (also known as dosage forms) can be contemplated.

The advantage of a coupled or combined galenic form also provides simplicity of treatment, patient compliance with the simplified treatment and therefore a more successful outcome.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polvinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

Examples of disintegrating agents include, but are not limited to, complex silicates, crosscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention and the list provided herein is not exhaustive.

Matrix Based Dosage Forms

Dosage forms according to one embodiment of the present invention may be in the form of coated or uncoated matrices. The term matrix, as used herein, is given its well known meaning in the pharmaceutical arts as a solid material having an active agent (e.g., the components of the compositions of the invention) of the invention incorporated therein. Upon exposure to a dissolution media, channels are formed in the solid material so that the active agent can escape.

The skilled artisan will appreciate that the matrix material can be chosen from a wide variety of materials which can provide the desired dissolution profiles. Materials can include, for example, one or more gel forming polymers such as polyvinyl alcohol, cellulose ethers including, for example, hydroxypropylalkyl celluloses such as hydroxypropyl cellulose, hypromellose, prop-2-enoic acid, hydroxypropyl methyl cellulose, hydroxyalkyl celluloses such as hydroxypropyl cellulose, natural or synthetic gums such as guar gum, xanthum gum, and alginates, as well as ethyl cellulose, polyvinyl pyrrolidone, fats, waxes, polycarboxylic acids or esters such as the Carbopol R series of polymers, methacrylic acid copolymers, and methacrylate polymers.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Methods of making matrix dosages are well known in the art and any known method of making such dosages which yields the desired immediate release and controlled release dissolution profiles can be used. One such method involves the mixture of the compositions of the invention with a solid polymeric material and one or more pharmaceutically acceptable excipients which can then be blended and compressed in controlled release tablet cores. Such tablet cores can be used for further processing as bi-layer or multilayer tablets, press coated tablets, or film coated tablets.

In addition, the formulation of respective release components can occur by appropriate granulation methods as is well known in the art. In wet granulation, solutions of the binding agent can be added with stirring to the mixed powders. The powder mass can be wetted with the binding solution until the mass has the consistency of damp snow or brown sugar. The wet granulated material can be forced through a sieving device. Moist material from the milling step can be dried by placing it in a temperature controlled container. After drying, the granulated material can be reduced in particle size by passing it through a sieving device. Lubricant can be added, and the final blend can then be compressed into a matrix dosage form such as a matrix tablet.

In fluid-bed granulation, particles of inert material and/or active agent (e.g., the components of the compositions of the invention) can be suspended in a vertical column with a rising air stream. While the particles are suspended, a common granulating material in solution can be sprayed into the column. There will be a gradual particle buildup under a controlled set of conditions resulting in tablet granulation. Following drying and the addition of lubricant, the granulated material will be ready for compression.

In dry-granulation, the active agent (e.g., the components of the compositions of the invention), binder, diluent, and lubricant can be blended and compressed into tablets. The compressed large tablets can be comminuted through the desirable mesh screen by sieving equipment. Additional lubricant can be added to the granulated material and blended gently. The material can then be compressed into tablets.

Particle Based Dosage Forms

Immediate Release and Controlled Release Particles

Dosage forms according to another embodiment of the present invention may be in the form of coated or uncoated immediate release/controlled release dosage forms. The immediate release/controlled release dosage forms of the present invention can take the form of pharmaceutical particles. The dosage forms can include immediate release particles in combination with controlled release particles in a ratio sufficient to deliver the desired dosages of active agents (e.g., the components of the compositions of the invention). The controlled release particles can be produced by coating the immediate release particles with an enteric coat.

The particles can be produced according to any of a number of well known methods for making particles. The immediate release particles can comprise the active agent combination (the compositions of the invention) and a disintegrant. Suitable disintegrants can include, for example, starch, low-substitution hydroxypropyl cellulose, croscarmellose sodium, calcium carboxymethyl cellulose, hydroxypropyl starch, and microcrystalline cellulose.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Particles can assume any standard structure known in the pharmaceutical arts. Such structures can include, for example, matrix particles, non-pareil cores having a drug layer and active or inactive cores having multiple layers thereon. A controlled release coating can be added to any of these structures to create a controlled release particle.

The term particle as used herein means a granule having a diameter of between about 0.01 mm and about 5.0 mm, preferably between about 0.1 mm and about 2.5 mm, and more preferably between about 0.5 mm and about 2 mm. The skilled artisan will appreciate that particles according to the present invention can be any geometrical shape within this size range and so long as the mean for a statistical distribution of particles falls within the particle sizes enumerated above, they will be considered to fall within the contemplated scope of the present invention.

The release of the therapeutically active agent (e.g., the components of the compositions of the invention) from the controlled release formulation of the present invention can be further influenced, i.e., adjusted to a desired rate, by the addition of one or more release-modifying agents. The release-modifying agent may be organic or inorganic and include materials that can be dissolved, extracted, or leached from the coating in the environment of use. The pore-formers may comprise one or more hydrophilic materials such as hydroxypropyl methylcellulose. The release-modifying agent may also comprise a semi-permeable polymer. In certain preferred embodiments, the release-modifying agent is selected from hydroxypropyl methylcellulose, lactose, metal stearates, and mixtures thereof.

The controlled release particles of the present invention can slowly release the compositions of the invention when ingested. The controlled release profile of the formulations of the present invention can be altered, for example, by increasing or decreasing the thickness of a retardant coating, i.e., by varying the amount of overcoating. The resultant solid controlled release particles may thereafter be placed in a gelatin capsule in an amount sufficient to provide an effective controlled release dose when ingested and contacted by an environmental fluid, e.g., gastric fluid, intestinal fluid or dissolution media.

The dosage forms of the invention may be coated (e.g., film coated or enterically coated) as known by those of skill in the art. For example, the composition can be formulated in an enteric coating that maintains its integrity in the stomach and releases the active compound in the intestine.

Examples of enteric-coatings include, but are not limited to, phenylsalicylate, fatty acids, fats, waxes, shellac, ammoniated shellac and cellulose acetate phthalates. Film coatings include, but are not limited to, hydroxyethylcellulose, sodium carboxymethylcellulose, polyethylene glycol 4000 and cellulose acetate phthalate.

In one example, the dosage forms e.g., particles of the invention as described above, may be overcoated with an aqueous dispersion of a hydrophobic or hydrophilic material to modify the release profile. The aqueous dispersion of hydrophobic material preferably further includes an effective amount of plasticizer, e.g. triethyl citrate. Preformulated aqueous dispersions of ethylcellulose, such as AQUACOAT™ or SURELEASE™ products, may be used.

The hydrophobic material may be selected from the group consisting of alkylcellulose, acrylic and methacrylic acid polymers and copolymers, shellac, zein, fatty oils, hydrogenated castor oil, hydrogenated vegetable oil, or mixtures thereof. In certain preferred embodiments, the hydrophobic material can be a pharmaceutically acceptable acrylic polymer including, but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylicacid alkylamine copolymer, poly(methyl methacrylate), poly(methacrylic acid anhydride), polymethacrylate, polyacrylamide, poly (methacrylic acid anhydride), and glycidyl methacrylate copolymers. In alternate embodiments, the hydrophobic material can be selected from materials such as one or more hydroxyalkyl celluloses such as hydroxypropyl methycellulose. The hydroxyalkyl cellulose can preferably be a hydroxy ($C_1$ to $C_6$) alkyl cellulose, such as hydroxypropylcellulose, hydroxypropylmethylcellulose, or preferably hydroxyethylcellulose. The amount of the hydroxyalkyl cellulose in the present oral dosage form can be determined, in part, by the precise rate of active agents (e.g., the components of the compositions of the invention) desired.

In embodiments of the present invention where the coating comprises an aqueous dispersion of a hydrophobic polymer, the inclusion of an effective amount of a plasticizer in the aqueous dispersion of hydrophobic polymer can further improve the physical properties of the film. For example, because ethylcellulose has a relatively high glass transition temperature and does not form flexible films under normal coating conditions, it may be necessary to plasticize the ethylcellulose before using it as a coating material. Generally, the amount of plasticizer included in a coating solution can be based on the concentration of the film-former, e.g., most often from about 1 percent to about 50 percent by weight of the film-former. Concentration of the plasticizer, however, can be preferably determined after careful experimentation with the particular coating solution and method of application.

Examples of suitable plasticizers for ethylcellulose include water-insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate may be an especially preferred plasticizer for the aqueous dispersions of ethyl cellulose of the present invention.

Examples of suitable plasticizers for the acrylic polymers of the present invention include, but are not limited to, citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as EUDRAGIT™ RL/RS lacquer solutions include polyethylene glycols, propylene glycol, diethyl phthalate, castor oil, and triacetin. Triethyl citrate may be an especially preferred plasticizer for aqueous dispersions of ethyl cellulose. It has further been found that addition of a small amount of talc may reduce the tendency of the aqueous dispersion to stick during processing and acts a polishing agent.

One commercially available aqueous dispersion of ethylcellulose is the AQUACOAT™ product which is prepared by dissolving the ethylcellulose in a water-immiscible organic solvent and then emulsifying the ethylcellulose in water in the presence of a surfactant and a stabilizer. After homogenization to generate submicron droplets, the organic solvent can be evaporated under vacuum to form a pseudolatex. The plasticizer will not be incorporated into the pseudolatex during the manufacturing phase. Thus, prior to using the pseudolatex as a coating, the AQUACOAT™ product can be mixed with a suitable plasticizer.

Another aqueous dispersion of ethylcellulose is commercially available as SURELEASE™ product (Colorcon, Inc., West Point, Pa., U.S.A.). This product can be prepared by incorporating plasticizer into the dispersion during the manufacturing process. A hot melt of a polymer, plasticizer (dibutyl sebacate), and stabilizer (oleic acid) can be prepared as a homogeneous mixture which can then be diluted with an alkaline solution to obtain an aqueous dispersion which can be applied directly onto substrates.

In one embodiment, the acrylic coating can be an acrylic resin lacquer used in the form of an aqueous dispersion, such as that which is commercially available from Rohm Pharma under the trade name EUDRAGIT™. In additional embodiments, the acrylic coating can comprise a mixture of two acrylic resin lacquers commercially available from Rohm Pharma under the trade names EUDRAGIT™ RL 30 D and EUDRAGIT™ RS 30 D. EUDRAGIT™ RL 30 D and EUDRAGIT™ RS 30 are copolymers of acrylic and methacrylic esters with a low content of quaternary ammonium groups, the molar ratio of ammonium groups to the remaining neutral (meth)acrylic esters being 1:20 in EUDRAGIT™ RL 30 and 1:40 in EUDRAGIT™ RS 30 D. The mean molecular weight is about 150,000 Daltons. The code designations RL (high permeability) and RS (low permeability) refer to the permeability properties of these agents. EUDRAGIT™ RL/RS mixtures are insoluble in water and in digestive fluids; however, coatings formed from them are swellable and permeable in aqueous solutions and digestive fluids.

The EUDRAGIT™ RL/RS dispersions may be mixed together in any desired ratio in order to ultimately obtain a controlled-release formulation having a desirable dissolution profile. Desirable controlled-release formulations may be obtained, for instance, from a retardant coating derived from one of a variety of coating combinations, such as 100% EUDRAGIT™ RL; 50% EUDRAGIT™ RL and 50% EUDRAGIT™ RS; or 10% EUDRAGIT™ RL and EUDRAGIT™ 90% RS. Of course, one skilled in the art will recognize that other acrylic polymers may also be used, for example, others under the EUDRAGIT™ brand. In addition to modifying the dissolution profile by altering the relative amounts of different acrylic resin lacquers, the dissolution profile of the ultimate product may also be modified, for example, by increasing or decreasing the thickness of the retardant coating.

The stabilized product may be obtained by subjecting the coated substrate to oven curing at a temperature above the Tg (glass transition temperature) of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 1 to about 48 hours. It is also contemplated that certain products coated with the controlled-release coating of the present invention may require a curing time longer than 24 to 48 hours, e.g., from about 48 to about 60 hours or more.

The coating solutions preferably contain, in addition to the film-former, plasticizer, and solvent system (i.e., water), a colorant to provide elegance and product distinction. Color may be added to the solution of the compositions of the invention instead of, or in addition to the aqueous dispersion of hydrophobic material. For example, color may be added to an AQUACOAT™ product via the use of alcohol or propylene glycol based color dispersions, milled aluminum lakes and opacifiers such as titanium dioxide by adding color with shear to the water soluble polymer solution and then using low shear to the plasticized AQUACOAT™ product.

Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retardant effect of the coating.

Spheroids or beads coated with the compositions of the invention can be prepared, for example, by dissolving the compositions of the invention in water and then spraying the solution onto a substrate, for example, non pareil 18/20 beads, using a Wuster insert. Optionally, additional ingredients can also be added prior to coating the beads in order to assist the binding of the compositions of the invention to the beads, and/or to color the solution, etc. For example, a product which includes hydroxypropyl methycellulose with or without colorant (e.g., OPADRY™ product, commercially available from Coloron, Inc.) may be added to the solution and the solution mixed (e.g., for about 1 hour) prior to application onto the beads. The resultant coated substrate, beads in this example, may then be optionally overcoated with a barrier agent to separate the compositions of the invention from the hydrophobic controlled release coating. An example of a suitable barrier agent is one which comprises hydroxypropyl cellulose. However, any film-former known in the art may be used. It is preferred that the barrier agent does not affect the dissolution rate of the final product.

Immediate release particles according to the present invention may be coated with a controlled release coating in order to change the release rate to obtain the dissolution rates according to the present invention.

Press Coated, Pulsatile Dosage Form

In another embodiment of the present invention, the compositions of the invention can be administered via a press coated pulsatile drug delivery system suitable for oral administration with a controlled release component, which contains a compressed blend of an active agent (e.g., the components of the compositions of the invention) and one or more polymers, substantially enveloped by an immediate release component, which contains a compressed blend of the active agent and hydrophilic and hydrophobic polymers. The immediate-release component preferably comprises a compressed blend of active agent and one or more polymers with disintegration characteristics such that the polymers disintegrate rapidly upon exposure to the aqueous medium.

The controlled-release component preferably can comprise a combination of hydrophilic and hydrophobic polymers. In this embodiment, once administered, the hydrophilic polymer will dissolve away to weaken the structure of the controlled-release component, and the hydrophobic polymer will retard the water penetration and help to maintain the shape of the drug delivery system.

In accordance with the present invention, the term "polymer" includes single or multiple polymeric substances, which can swell, gel, degrade or erode on contact with an aqueous environment (e.g., water). Examples include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, pregelaiinized starch, shellac, and zein, and combinations thereof.

The term "hydrophilic polymers" as used herein includes one or more of carboxymethylcellulose, natural gums such as guar gum or gum acacia, gum tragacanth, or gum xanthan, hydroxyethyl cellulose, hydroxypropyl cellulose, hydroxypropyl methylcellulose, methylcellulose, and povidone, of which hydroxypropyl methylcellulose is further preferred. The term "hydrophilic polymers" can also include sodium carboxymethycellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal or alkaline earth metal, carageenate alginates, ammonium alginate, sodium alganate, or mixtures thereof.

The hydrophobic polymer of the drug delivery system can be any hydrophobic polymer which will achieve the goals of the present invention including, but not limited to, one or more polymers selected from carbomer, carnauba wax, ethylcellulose, glyceryl palmitostearate, hydrogenated castor oil, hydrogenated vegetable oil type 1, microcrystalline wax, polacrilin potassium, polymethacrylates, or stearic acid, of which hydrogenated vegetable oil type 1 is preferred. Hydrophobic polymers can include, for example, a pharmaceutically acceptable acrylic polymer, including, but not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH dependent.

The present invention also provides a method for preparing a press coated, pulsatile drug delivery system comprising the compositions of the invention suitable for oral administration. This method can include the steps of combining an effective amount of the components of the compositions of the invention, or a pharmaceutically acceptable salt thereof, and a polymer to form an immediate-release component; combining an effective amount of an active agent (e.g., the components of the compositions of the invention), or a pharmaceutically acceptable salt thereof, and a combination of hydrophilic and hydrophobic polymers to form a controlled release component; and press coating the controlled-release component to substantially envelop the immediate release component.

A preferred embodiment further can include the steps of combining an effective amount of an active agent (e.g., the components of the compositions of the invention), or a pharmaceutically acceptable salt thereof, and a polymer to form an immediate release component, and press coating the immediate release component to substantially envelop the controlled release component. In another preferred embodiment, the combining steps can be done by blending, wet granulation, fluid-bed granulation, or dry granulation according to methods recognized in the art.

The agents of the invention can also be mixed with other active materials which do not impair the desired action, or with materials that supplement the desired action, such as antacids, H2 blockers and anti-inflammatory agents. Higher concentrations, up to about 98% by weight of the components of the compositions of the invention may be included.

The dosage form of the invention may be administered to mammalian subjects, including: humans, monkeys, apes, dogs, cats, cows, horses, rabbits, pigs, mice and rats.

The dosage form of the invention may be administered orally (e.g., in liquid form within a solvent such as an aqueous or non-aqueous liquid, or within a solid carrier), rectally, parenterally, intracisternally, intravaginally, intraperitoneally, topically (as by powders, ointments, lotion, gels, drops, transdermal patch or transcutaneous patch), bucally, in bronchial form or as an oral or nasal spray. The term "parenteral" as used herein refers to modes of administration which include intravenous (e.g., within a dextrose or saline solution), intramuscular, intrasternal, subcutaneous, intracutaneous, intrasynovial, intrathecal, periostal, intracerebroventricularly, intra-articular injection and/or infusion. Alternative methods include administration by pump or continuous infusion, injection (e.g., as a suspension or as an emulsion in a pharmaceutically acceptable liquid or mixture of liquids), or liposomes. Administration can be performed daily, weekly, monthly, every other month, quarterly or any other schedule of administration as a single dose injection or infusion, multiple doses, or in continuous dose form. The administration of the pharmaceutical compositions of the present invention can be intermittent or at a gradual, continuous, constant or controlled rate to a subject. In addition, the time of day and the number of times per day that dosage form(s) is administered can vary.

For parenteral administration, in one embodiment, the agents of the invention can be formulated generally by mixing it at the desired degree of purity, in a unit dosage injectable form (solution, suspension, or emulsion), with a pharmaceutically acceptable carrier(s) described above.

Any dosage form used for therapeutic administration should be sterile. Sterility can readily be accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

The appropriate dose of the compound will be that amount effective to prevent occurrence of the symptoms of arthritis from which the patient suffers. By "effective amount", "therapeutic amount" or "effective dose" is meant that amount sufficient to elicit the desired pharmacological or therapeutic effects, thus resulting in effective prevention or treatment of an arthritic disorder or condition. Prevention or amelioration of the arthritic disorder or condition can be manifested by delaying the onset of the symptoms of the arthritic disorder or condition. Treatment of the disorder can be manifested by a decrease in the symptoms associated with the arthritic disorder or condition or an amelioration of the recurrence of the symptoms of the arthritic disorder or condition.

Kits

The invention further provides a kit comprising a device suitable for use according to the instant invention, for example, in local delivery, including direct injection of a therapeutic agent to the joint to treat arthritis and/or diseases involving cartilage degeneration. The device may be prepackaged in a sterile container ready for use. The kit may further include a therapeutic agent and other substances needed to prepare the final composition to be used to treat arthritis and/or diseases involving cartilage degeneration. In an embodiment, the kit includes unit doses of the therapeutic agent in injectable form. Unit dosage forms for injection may comprise the therapeutic agent in a composition as a solution in sterile water, normal saline, or another pharmaceutically acceptable carrier. In an embodiment, the kit includes unit doses of a therapeutic agent for treating arthritis and/or diseases involving cartilage degeneration in a patient, for example, any one or more of the anabolic factors of the invention In an embodiment, the kit includes instructions for its use. These instructions may describe the attendant benefits of the therapeutic agent in treating arthritis and/or diseases involving cartilage degeneration and may be provided in a variety of forms. Suitable forms include printed information, a compact disc, and the like. Suitable devices, including catheters; therapeutic agents; and unit doses are those described herein.

Methods of the Invention

The present invention also provides methods for treating proteoglycan deficiency in a subject comprising administering to the subject any of the compositions of the invention comprising at least a first therapeutic agent, wherein the first therapeutic agent comprises one or more anabolic factors of the invention that promotes proteoglycan synthesis. The method can further comprise administering any of the proteoglycan synthesis modulator of the invention to the subject.

The present invention also provides methods for inducing cartilage synthesis and/or repair in a subject comprising administering to the subject any of the compositions of the invention comprising at least a first therapeutic agent, wherein the first therapeutic agent comprises one or more anabolic factors of the invention that promotes proteoglycan synthesis. The method can further comprise administering any of the proteoglycan synthesis modulator of the invention to the subject.

The present invention also provides methods for treating arthritis and/or diseases involving cartilage degeneration in a subject comprising administering to the subject any of the compositions of the invention comprising at least a first therapeutic agent, wherein the first therapeutic agent comprises one or more anabolic factors of the invention that promotes proteoglycan synthesis. The method can further comprise administering any of the proteoglycan synthesis modulator of the invention to the subject. The arthritis can be any of osteoarthritis, rheumatoid arthritis, lupus-associated arthritis, juvenile idiopathic arthritis, reactive arthritis, enteropathic arthritis and psoriatic arthritis. Further, diseases involving cartilage degeneration can be any disorder, syndrome, disease, and/or injury that affect spinal discs or joints in animals, including humans, e.g., articular joints, and include, but are not limited to, chondrophasia, sponylarthropathy, ankylosing spondylitis, lupus erythmatosus, relapsing polychondritis, and Sjogren's syndrome.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

Example 1

Isolation of Cartilage from Bovine Metacarpal Phalangeal Joints

Cartilage was obtained from Articular Engineering (Northbrook, Ill.) which harvested and processed the cartilage from bovine metacarpal phalangeal joints following procedures established by Koichi Masuda and Robert L. Sah, as described in Chapter 7: Tissue Engineering of Articular Cartilage in *Culture of Cells for Tissue Engineering,* ed. by G. Vunjak-Novakovic & R. I. Freshney (Wiley, Inc. 2004).

Example 2

Isolation of Chondrocytes from Cartilage and Primary Culture (Passage P0)

Chondrocytes were isolated from the cartilage harvested and shipped by Articular Engineering (Northbrook, Ill.) to us overnight at 4° C. in chondrocyte culture media which contained DMEM/F12 (50:50 mix, Mediatech, Herndon, Va.), 10% Fetal Bovine Serum (FBS, Mediatech), 50 microgram (n)/milliliter (ml) of gentamycin (Invitrogen, Carlsbad, Calif.), 360 ug/ml of L-Glutamine (Mediatech) and 25 µg/ml of Ascorbic acid (St. Louis, Mo.). The cartilage was stored at 4° C. in the chondrocyte culture media and processed within 48 hours (hr) of arrival.

Chondrocytes were isolated from the cartilage by a two-step digestion. The first step was a 1.5 hr Pronase digestion in a Pronase enzyme digestion solution containing the following media: 0.2% Pronase (Calbiochem, San Diego, Calif.) in DMEM/F12 (50:50 mix; Mediatech) supplemented with 50 μg/ml of gentamicin (Invitrogen, Carlsbad, Calif.) and 360 ug/ml of L-glutamine (Mediatech). This solution was prepared fresh approximately 20 minutes (min) before use and filtered in a 0.2 micron filter before use. Fifty ml of the Pronase enzyme digestion solution was added for each 8 grams (g) of tissue in a 200 ml sample cup (VWR, West Chester, Pa.) and incubated for 1.5 hr with gentle stirring at 37° C. in a 5% $CO_2$ tissue culture incubator. At the end of the Pronase enzyme digestion incubation period, the cartilage was washed three times, for 2 min each time, with 50 ml of sterile DMEM/F12 (50:50 mix, Mediatech) supplemented with 50 μg/ml of gentamicin (Invitrogen) and 360 g/ml of L-glutamine media (Mediatech).

Following the Pronase digestion step, the cartilage tissue was digested in a second step with Collagenase-P in a Collagenase-P enzyme digestion solution containing 0.025% Collagenase-P (Roche Diagnostics, Basel, Switzerland) in DMEM/F12 (50:50 mix, Mediatech) supplemented with 5% FBS (Mediatech), 50 μg/ml of gentamicin (Invitrogen), 360 μg/ml of L-glutamine (Mediatech), and 25 μg/ml of ascorbic acid (Sigma). This solution was prepared fresh approximately 20 min before use and filtered in a 0.2 micron filter before use. Fifty ml of the Collagenase-P enzyme digestion solution was added for each 8 g of tissue in a 200 ml sample cup (VWR, West Chester, Pa.) and incubated for 16 hr with gentle stirring at 37° C. in a 5% $CO_2$ tissue culture incubator.

Following Collagenase-P digestion incubation period, the resulting cell suspension was filtered through a 40 micron filter cup (VWR) to remove undigested tissue. The filtered cell suspension, containing the isolated chondrocytes, was washed three times, for 2 min each time, with 50 ml of sterile DMEM/F12 (50:50 mix, Mediatech) supplemented with 50 μg/ml of gentamicin (Invitrogen) and 360 g/ml of L-glutamine media (Mediatech).

The isolated and washed chondrocytes, referred to herein as "primary chondrocytes," were plated at a high density of approximately $2.5 \times 10^5$/centimeter square ($cm^2$) in a plastic cell culture flask (BD Falcon, Bedford Mass.). This plating was referred to as the P0 passage or P0. Primary chondrocyte culture exhibited a 'cobblestone' morphology as shown in FIG. 1A. This cobblestone morphology was considered a good indicator that the chondrocytes had maintained their phenotype and had not differentiated into fibroblasts.

Example 3

Passage of Chondrocyte Monolayers (Passage P1)

Initially, primary chondrocyte monolayer cells (P0) were cultured for five to six days prior to use in a high throughput assay using 96 well microtiter plates. However, during this time, the chondrocytes engaged in abundant extracellular matrix synthesis which resulted in detachment of the monolayer of chondrocytes from the bottom of the 96 well microtiter cell culture plates. This detachment was a major limitation for use of P0 chondrocytes in high throughput screening (described below). We found that P0 chondrocytes that were passaged once to produce single passage cells (P1 cells) yielded a better quality monolayer culture than the P0 cells in terms of better adherence of cells to the bottom of the 96 well microtiter cell culture plates. P 1 cells also responded with higher sensitivity in proteoglycan synthesis to stimulus such as IGF-1 than did the parental P0 cells (described in Example 6). Passage of primary P0 chondrocytes was conducted in the following manner: After 5-6 days of culture, the P0 monolayers were washed with DPBS (Mediatech) and gently harvested with 0.5 mM EDTA (Sigma) treatment for 10 min at 37° C. in a 5% $CO_2$ tissue culture incubator. After 10 min of incubation, Trypsin-EDTA (Mediatech) was added to a final concentration of 0.125% and the monolayers were incubated at 37° C. in a 5% $CO_2$ tissue culture incubator for 2-3 min. Following trypsinization, cells were washed once with DPBS (Mediatech) and resuspended in chondrocyte culture media. Cells were plated in chondrocyte culture media at a seeding density of about 150,000 cells per well in 96 well cell culture plate (BD Falcon, Bedford Mass.). These cells were allowed to grow to produce a monolayer of P1 cells.

Example 4

Phenotypic Characterization of Passage 1 (P1) Chondrocyte Monolayers

Phenotypic characterization of passage 1 (P1) chondrocyte monolayers was done by three different methods to ensure that the chondrocyte monolayers did not de-differentiate into fibroblasts after the P0 stage.

The first method was microscopic examination of monolayers. As shown in FIG. 1B, P1 monolayers retained the 'cobblestone' morphology seen in P0 monolayers (FIG. 1A). This 'cobblestone' morphology was accepted as an indicator of chondrocytic phenotype. Repeated passage of chondrocytes to P4 passage resulted in de-differentiation of chondrocytes to fibroblasts as shown in FIG. 1C, where the cells no longer exhibited a 'cobblestone' morphology but instead had become elongated and resembled fibroblasts. The P4 cells shown in FIG. 1C had been passaged 3 additional times in the same manner as the original P1 passage.

The second method to determine chondrocyte phenotype was size analysis of synthesized proteoglycans. We observed that chondrocytes primarily synthesized large proteoglycans while de-differentiated chondrocytes synthesized primarily smaller sized proteoglycans.

For this experiment, Koichi Masuda (Rush University, Chicago, Ill.) isolated, cultured and passaged cells as described above. Analysis of the proteoglycan size was done in Koichi Masuda's laboratory using protocols described in Mok, S. S. et al. (1994) J. Biol. Chem. 269(No. 52):33021-33027. Briefly, cells were placed in chondrocyte starvation media for 24 hr and then placed in chondrocyte treatment media for 24 hr. Treatment media consisted of DMEM/F12 (50:50 mix, Mediatech), 50 μg/ml of gentamicin (Invitrogen), 360 μg/ml of L-glutamine (Mediatech), 25 μg/ml of ascorbic acid (Sigma) and 2.5% FBS (final concentration, Mediatech). Samples were stimulated with 100 ng/ml of recombinant IGF-1 (R&D Systems, Minneapolis, Minn.) for proteoglycan synthesis and newly synthesized proteoglycans were labeled using [$^{35}$S] sulfate incorporation. Analysis of newly synthesized proteoglycan was then performed by Sepharose CL-2B column chromatography which separated molecules according to their molecular size and their charge. Briefly, fractions (approximately 1.0 ml) were collected and aliquots assayed for radioactivity by liquid scintillation counting. The partition coefficient of the proteoglycans in each column fraction was determined according to established methodologies in the Masuda laboratory. The results indicated that the P1 passage chondrocytes synthesized proteoglycans with the same partition coefficient as that of the P0 passage chondrocytes described in Mok, et al. (1994). This study indicated that the proteoglycans synthesized by the P0 and P1 cultures were similar with respect to sizes and charges.

The third method to determine chondrocyte phenotype was to determine the type of collagen synthesized by the P1 passage cells. We understood that normal chondrocytes primarily synthesized type II collagen while de-differentiated chondrocytes, such as fibroblasts, present in many other tissues, primarily synthesized type I collagen, consistent with normal cartilage tissue being primarily composed of type II collagen (approximately 90% of the total collagen content) and, Type I collagen being typically present at undetectable levels in normal articular cartilage. Type II collagen is a homotrimer composed of a single type of alpha chain, $\alpha 1(II)$. Thus, when collagen type II was analyzed by SDS-PAGE, only a single band would be seen. In contrast, type I collagen is a heterotrimer, composed of two $\alpha 1(I)$ chains and one $\alpha 2(I)$ chain. The $\alpha 2(I)$ chain has a lower molecular weight than the $\alpha 1(I)$ chain. When type 1 collagen was analyzed by SDS-PAGE, two bands would be seen. This experiment was performed by Articular Engineering according to methods described in Miller, E. J. (1972), Biochem. 11(26):4903-9. Briefly, to determine the type of collagen produced by the P1 chondrocytes, medium from the P1 cell cultures were separated from any insoluble material by high-speed centrifugation. The resulting supernatant was precipitated with ammonium sulfate and resolubilized in a neutral buffered saline solution. Fifteen ug of protein each from this and other samples, including bovine type I collagen, bovine type II collagen, P1 cells treated for 24 h in chondrocyte treatment media with either 50 ng/ml or 100 ng/ml of IGF-1 (R&D Systems, Inc., Minneapolis, Minn.) and molecular weight standards was run on a 7.5% sodium dodecyl sulfate (SDS)-polyacrylamide gel (PAGE) under reducing conditions and stained with silver stain.

Our results showed that the passage P1 chondrocytes, both treated with recombinant IGF-1 (R&D Systems) and untreated, had gel banding profiles that most closely resembled the type II collagen profile and not the type I collagen profile.

Example 5

Development of High throughput Proteoglycan Synthesis Assay

Our goal was to develop a high throughput, automated assay that would allow us to identify factors that stimulated the anabolic function of chondrocytes, namely synthesis of proteoglycans (especially aggrecans) and collagen type II, the two key components of cartilage. We also wanted to develop an assay that would allow us to measure the total proteoglycans that were synthesized, both the proteoglycans that were secreted into the media as well as those deposited into the extracellular matrix. The assay we developed was successful in combining all of the above requirements and was based on combining two different technologies. The first technology allowed sensitive detection of new proteoglycan synthesis by using radioactive incorporation of $[^{35}S]$-sulfate into the sulfate moieties covalently attached to the glucosamine groups of the proteoglycans. The second technology allowed high-throughput measurement of the newly synthesized proteoglycans by capture on Alcian Blue (VWR, West Chester, Pa.) coated microtiter plates.

For the assay, P1 cells were plated at a concentration of 150,000 cells per well for 24 hr in 96 well plates in chondrocyte culture media using an automated 8 channel uFill cell dispenser (Bio-Tek, Winooski, Vt.) to form the monolayer. The cells were then serum starved for an additional 24 hr in chondrocyte culture media lacking FBS. The cells were then treated for 24 hr with either control or test compounds in treatment media (defined below). Both the starvation of cells and treatment was done using BioMek-FX automated 96 channel liquid handling system (Beckman Coulter, Fullerton, Calif.). Treatment media consisted of DMEM/F12 (50:50 mix, Mediatech), 50 µg/ml of gentamicin (Invitrogen), 360 ug/ml of L-glutamine (Mediatech), 25 µg/ml of ascorbic acid (Sigma) and 2.5% FBS (final concentration, Mediatech) plus any test compounds added to the sample. Treated monolayers were then incubated with 20 micro Curie (µcurie)/ml of $[^{35}S]$-sulfate in treatment media for 4-5 hr at 37° C. in a 5% $CO_2$ incubator.

Secreted proteoglycans were measured by transferring 100 µl of the media supernatant to Alcian Blue coated microtiter plates. To measure the extracellular matrix associated proteoglycans, the cells were washed twice gently with 200 µl per well of DPBS (Mediatech). This washing removed the free $[^{35}S]$-sulfate. Proteoglycans were extracted from the cells by overnight incubation of the monolayers at 60° C. with 150 µl of Papain (Sigma) to a final Papain concentration of 20 µg/ml in Papain extraction buffer. The Papain extraction buffer contained 0.1 M Sodium Acetate (Sigma), 0.05 M EDTA pH 5.53 (Sigma) and 5 mM L-Cysteine Hydrochloride hydrate (Sigma).

$[^{35}S]$-sulfate labeled proteoglycans in media and Papain digested cellular extracts were captured separately on Alcian blue coated plates. The Alcian blue capture method was modified from that described by Rees-Milton, K. J. and Anastassiades, T. P. (2003), Anal. Biochem. 315:273-276. Capture plates were prepared by treating opaque 96 well microtiter plates (Perkin Elmer, Wellesley, Mass.) for 60 min at 37° C. with 100 µl of a 1.0% Alcian Blue solution in 3% acetic acid. The Alcian Blue solution was then aspirated off the wells and the plates were air dried overnight in the dark at room temperature. Prior to use, the plates were washed twice with 300 µl of DPBS (Mediatech) and then air dried at room temperature for 30 min.

Example 6

Figure 2:
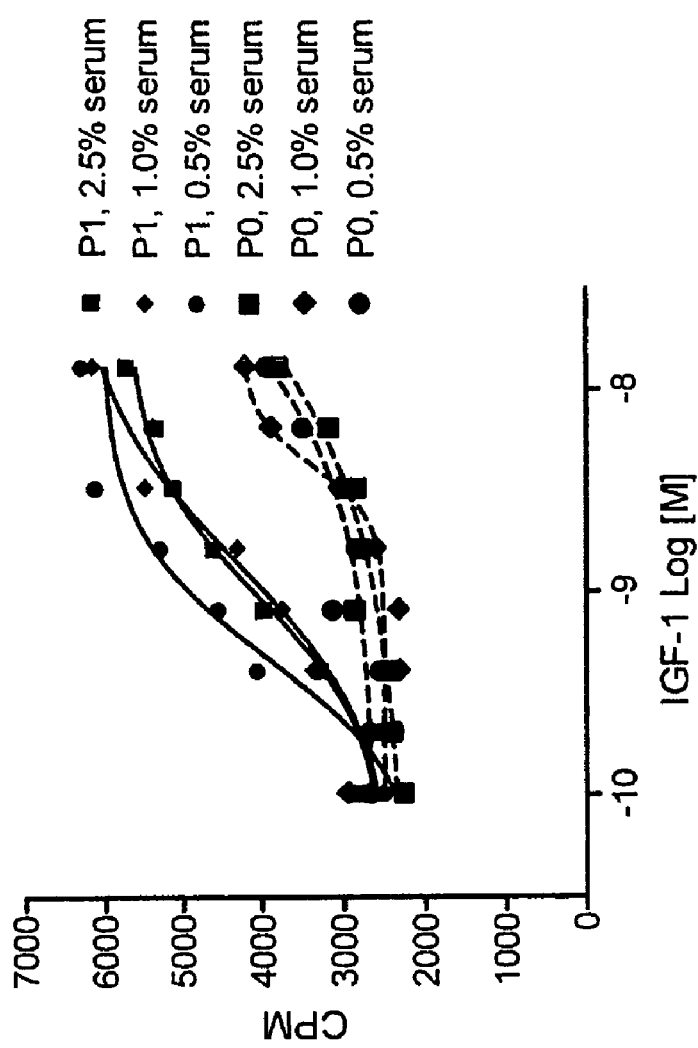
FIG. 2 is a graphical representation of the amount of proteoglycan synthesized by P0 or P1 chondrocytes in the presence of 0.5%, 1% or 2.5% of serum, as measured by incorporation of radioactivity (in CPM), as a function of the concentration of IGF-1 present (in log M).

Comparison of P0 and P1 Chondrocyte Monolayers with Respect to Proteoglycan Synthesis Using High throughput Proteoglycan Synthesis Assay Primary P0 versus P1 normal bovine chondrocytes monolayers were treated respectively with increasing concentrations of IGF-1 (R&D Systems) ranging from $10^{-10}$ M to $10^{-8}$ M, in 0.5%, 1.0% and 2.5% serum containing chondrocyte starvation media using the high throughput proteoglycan synthesis assay described in Example 5. Total $[^{35}S]$ sulphate incorporated in newly synthesized proteoglycans was measured in each sample. Results are shown in FIG. 2, which plots concentration of IGF-1 against the radioactivity (CPM) measured. As shown in FIG. 2, the P1 chondrocytes treated with IGF-1 in 0.5%, 1.0% or 2.5% serum incorporated a higher level of radioactivity than similarly treated P0 chondrocytes. These results demonstrated that the P1 chondrocytes were more responsive to IGF-1 stimulation than were the P0 chondrocytes and, thus, would be more suitable for use in high throughput screening.

Example 7

Comparison of Alcian Blue Capture Method to G-25 Column Chromatography

Figure 3:
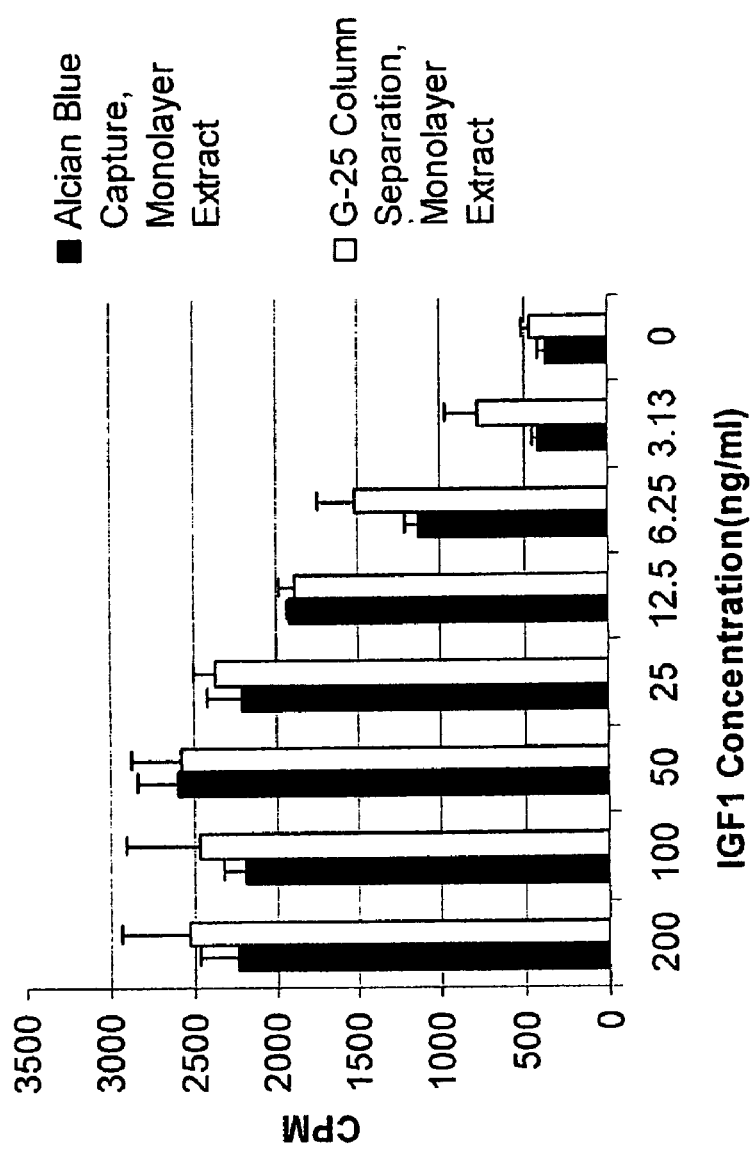
FIG. 3 is a graphical representation of the amount of proteoglycan synthesized and extracted from monolayers of chondrocytes, as measured by incorporation of radioactivity (in CPM), that was detected by the Alcian Blue Capture method and by the G-25 column separation method, in the presence of varying concentrations of IGF-1 (in ng/ml).

We compared the Alcian Blue capture method described above to a well-established method for analyzing the amount of labeled, sulfated proteoglycans. P1 chondrocytes were prepared, stimulated with varying doses of IGF-1 for 24 hr, pulse labeled and then analyzed for incorporation of radioactivity, as described above. Half the samples were then processed by the Alcian Blue plate method described above. The other half of the samples was analyzed by the well-established method of G-25 column chromatography. For the G-25 column method, a 96 column plate (Nest Group, Southboro, Mass.) was soaked in water to hydrate the beads. The columns were equilibrated with 3 washes of a buffer composed of 4 M guanidine hydrochloride, 0.05 M Sodium Acetate, 0.1 M Sodium Sulfate, 0.5% Triton-X100, pH 7.5 (all reagents from Sigma). Then the Papain digested samples were applied to the equilibrated columns and the columns centrifuged to separate the labeled proteoglycans from the bulk sample and any free label, which were retained by the column. Results are shown in FIG. 3, which showed the amount of radioactivity (in CPM) incorporated in the matrix of the P1 chondrocytes in relation to the amount of IGF-1 used (in ng/ml) to stimulate the cells. Results in FIG. 3 demonstrated that both methods were comparable in terms of absolute signal and signal-to-noise ratio. Stimulation of proteoglycan synthesis by IGF-1 was dose dependent, reaching a peak at about 50 ng/ml of IGF-1. However, the Alcian Blue method required approximately three to four times less labor and also cost approximately 10% of the cost of the G-25 method. In addition, the G-25 column method could not be used to analyze the proteoglycans secreted into the media because the volume of the media that was needed to be added (100 μl) exceeded the loading capacity of the columns (20 μl).

Example 8

Validation of the Proteoglycan Synthesis Assay for High throughput Screening

Figure 4:
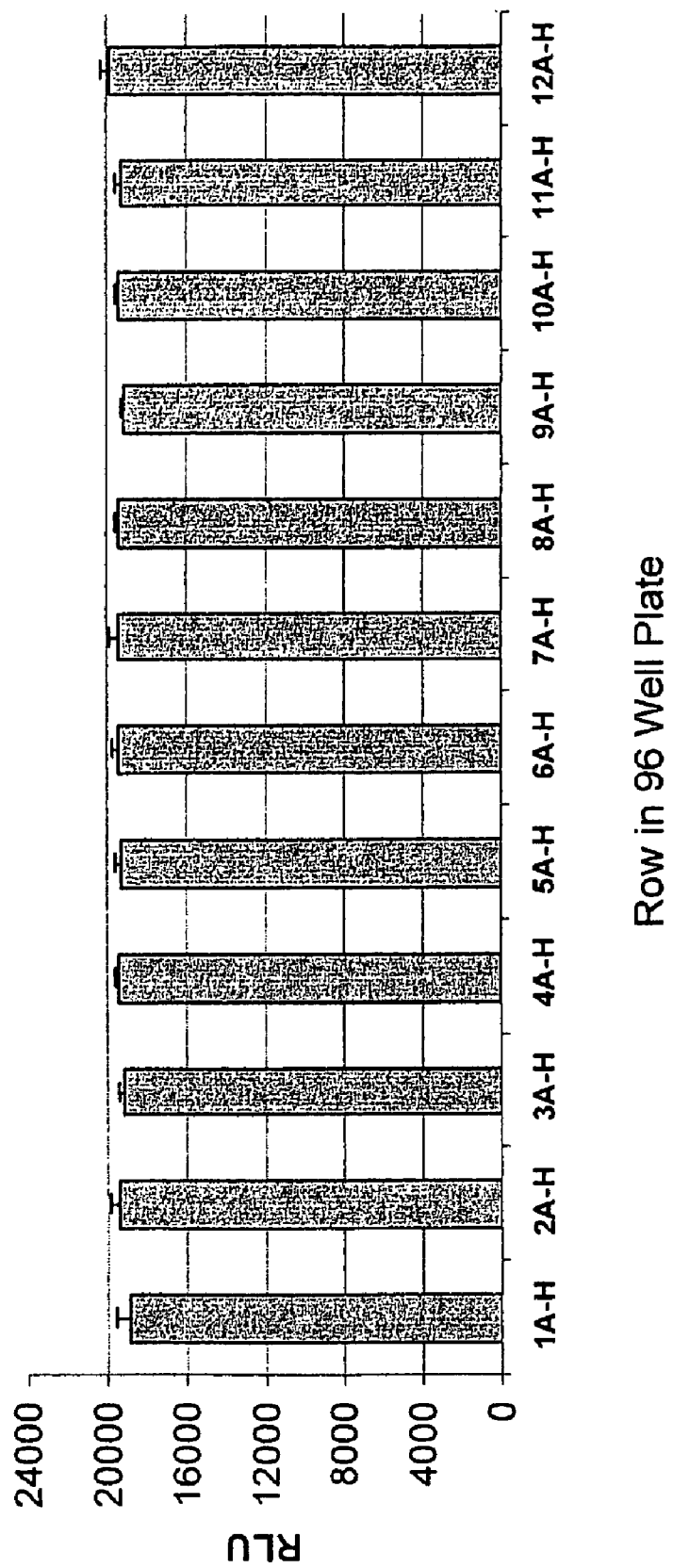
FIG. 4 is a graphical representation of plating accuracy and consistency among the different rows of a 96 well plate in detecting viability of cells (in RIX) as measured in a Cell Titer Glo assay that measured ATP levels.

To determine the accuracy of the Bio-Tek uFill cell dispensing protocol, we assayed P1 monolayers for ATP levels, which would be reflective of the number of viable cells, 24 hr after cells were dispensed. To measure ATP levels, we used the Cell Titer-Glo assay (Promega, Madison, Wis.) according to the manufacturer's instructions. ATP levels in the plated monolayers were measured by adding 100 μl of Cell Titer Glo reagent to the P1 monolayers that had been plated for 24 hours in chondrocyte culture media in 96 well plates. Each set of 12 wells from each row was then combined into single samples. Results are shown in FIG. 4, with relative light units (RLU) on the y-axis and the rows A through H on the x-axis. FIG. 4 shows that, the ATP levels reflected in RLU, and hence number of live cells, were uniformly the same (about 19,000 RLU) among the different rows, validating the use of the Bio-Tek uFill cell dispenser for use in the high throughput proteoglycan synthesis assay.

Figure 5:
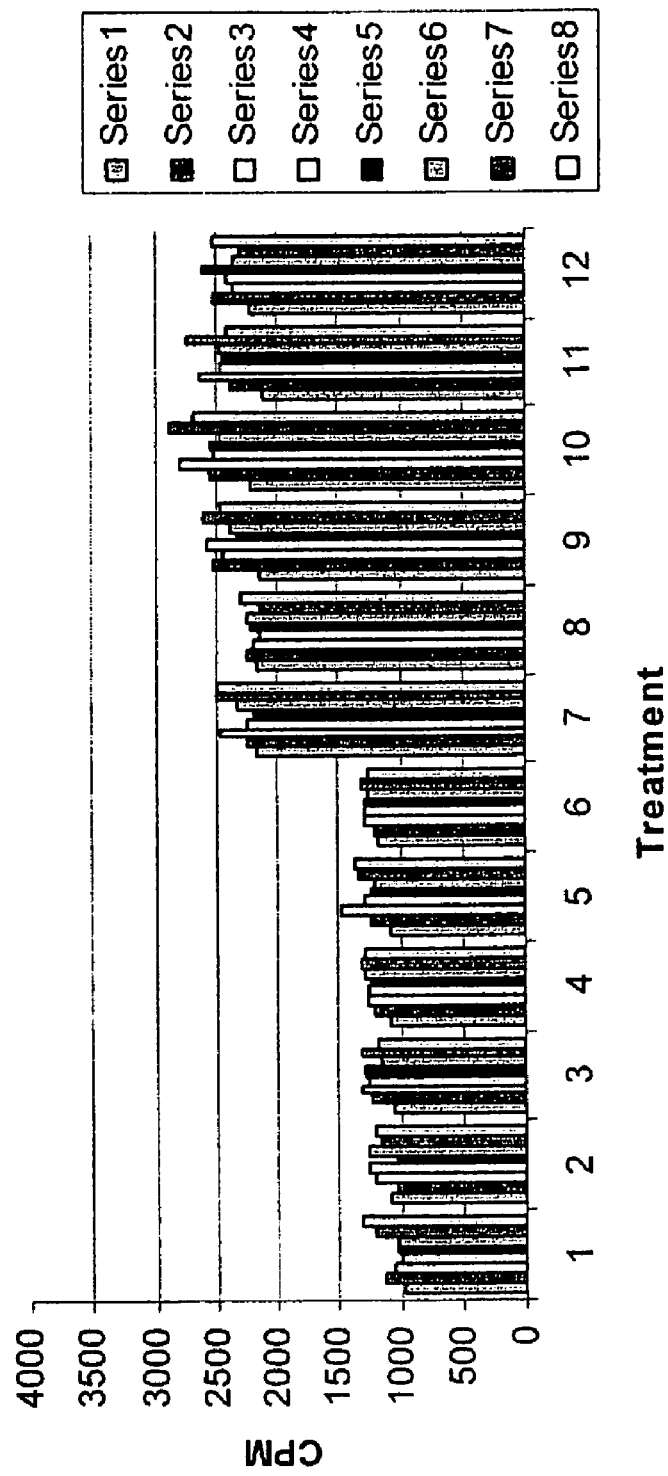
FIG. 5 is a graphical representation of the variance of the proteoglycan synthesis assay of IGF-1 treated and untreated P1 bovine chondrocytes determined through measurement of incorporation of radioactivity (in CPM). The numbers on the X-axis represent row numbers of the 96 well plate. Series 1 represents column A of the plate; Series 2 represents column B; Series 3 represents column C; Series 4 represents column D; Series 5 represents column E; Series 6 represents column F; Series 7 represents column G; and Series 8 represents column H.

To determine the variance of the proteoglycan synthesis assay, we assayed P1 monolayer cells treated with or without IGF-1 for 24 hr and then assayed as described in Example 5. Forty-eight samples in the 96-well plate were left untreated and 48 samples were treated with 100 ng/ml recombinant IGF-1 (R&D Systems). Results, shown in FIG. 5, established that the variance between individual samples was less then 20%, which would be suitable for high throughput screening. In addition, the signal-to-noise ratio (stimulated vs. unstimulated) was approximately 2.5-fold, which also rendered this measurement suitable for high throughput screening.

Example 9

High throughput Screening of Five Prime Therapeutics' Secreted Protein Library

The high throughput proteoglycan synthesis assay described in Example 5 was used to screen a protein library. This library contained approximately 3,500 human secreted proteins and soluble receptors, present in conditioned media in 44 80-well plates. Commercially available recombinant protein IGF-1 (R&D Systems, Inc.) was used as external control and internally produced IGF-1 and pro-insulin served as internal controls of the library's quality. Each member of the library was assayed at least two times in duplicate plates for activity.

Figure 6A:
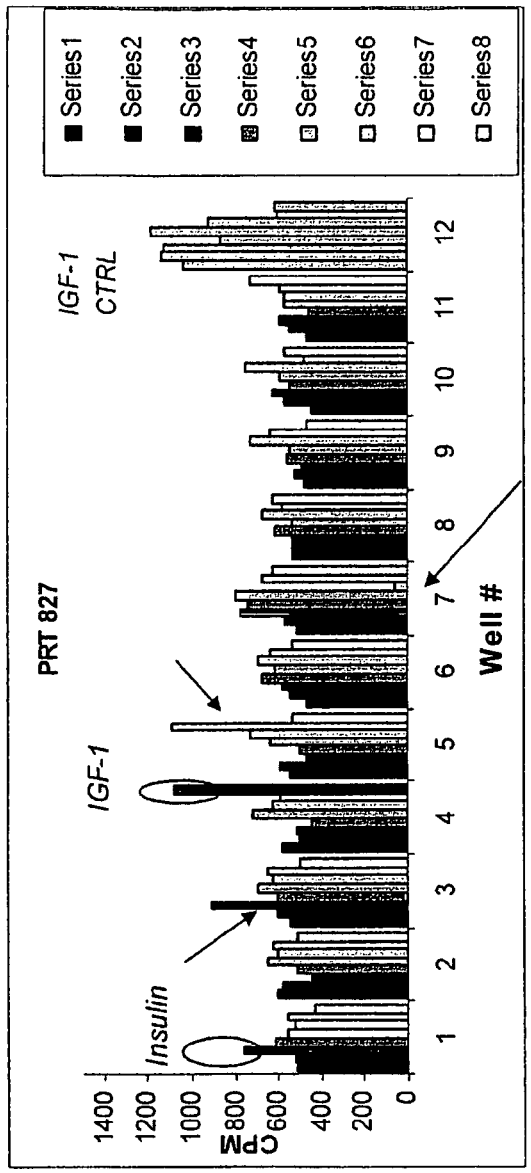
FIG. 6A represents results from one plate.
Figure 6B:
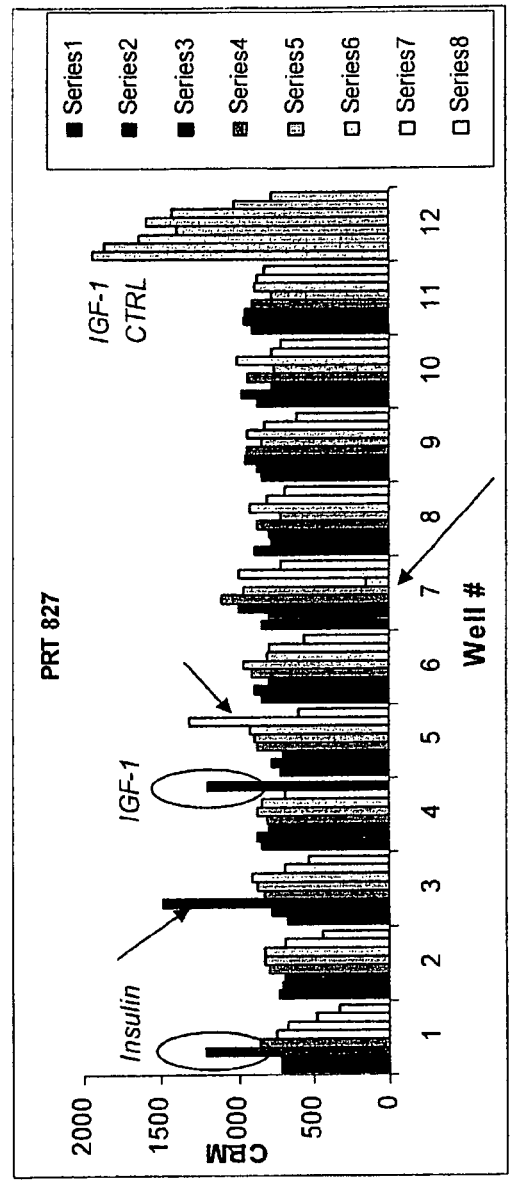
FIG. 6B represents results from a duplicate plate. The wells are as described in FIG. 5.

On average, approximately 8-16 protein plates were screened in duplicates per week. FIG. 6 is an example of such a screening result. Each well is identified by its column number and row location. The numbers 1 through 12 each represents the column number of the wells in the plate. Series 1 represents the wells in row A and is the first bar in each column; Series 2 represents the wells in row B and is the second bar in each column; Series 3 represents the wells in row C and is the third bar in each column; Series 4 represents the wells in row D and is the fourth bar in each column; Series 5 represents the wells in row E and is the fifth bar in each column; Series 6 represents the wells in row F and is the sixth bar in each colum; Series 7 represents the wells in row G and is the seventh bar in each column; and Series 8 represents the wells in row H and is the eighth bar in each column. The two duplicate plates are shown as FIG. 6A and FIG. 6B. The positive internal controls (IGF-1 and pro-insulin) are circled and the positive external controls (recombinant IGF-1 purchased from R&D Systems, Inc.) are shown as column 12 for both the first and duplicate plates. The recombinant IGF-1 was added at concentrations of 100 ng/ml into wells Al2, B12, C12 and D12, 33 ng/ml into well E12), 11 ng/ml into well F12, 3.3 ng/ml into well G 12, and 1.1 ng/ml into well H 12. Eighty test compounds from the library were tested for promotion of proteoglycan synthesis activity. FIGS. 6A & 6B each shows two compounds that promoted proteoglycan synthesis, that is, demonstrated anabolic activity, as indicated by the arrows pointing down, while one compound inhibited proteoglycan synthesis, that is, demonstrated catabolic activity, as indicated by the arrow pointing up. In the example shown, all controls and compounds with activity retained their activities in the duplicate plate. The high throughput screening data was analyzed in two ways. The first way calculated the standard deviation (sigma) from median for each test compound using the following formula:

Standard deviation from median(sigma)=[CPM (well)−[CPM(blank)]/sigma(blank).

where "CPM (well)" represented the measured CPM from a particular test compound well and CPM (blank) was calculated the following way. The median and the standard deviation of the raw value of the wells containing test compounds were calculated. For example, in the typical 80-compound plate layout, qualified wells were ranged from Column 2 to Column 11. Then, test compound wells with CPM values that were outside of median by plus or minus 2 standard deviations (sigma) were rejected. The remaining test compound wells were then used to recalculate a new median and a new standard deviation. The CPM (blank) was defined as the new, recalculated median value and the sigma (blank) was defined as the new, recalculated standard deviation.

The second way of analyzing primary screening data was using a rank sum analysis. The hit score for each clone was based on the p-value for the rank sum of a clone. Ranks for a clone were defined as follows:
1. Starting with a given clone, call it CLONE1, we identified all assay plates that contained CLONE1.
2. For an assay plate that contained CLONE1, we calculated the rank by counting the number of raw scores (i.e., CPM) on the plate that were less than CLONE1. For example, if 77 clones on the plate had scores that were less than CLONE1, the rank of CLONE1 on the plate would be 78.
3. We calculated the ranks for CLONE 1 on each of the assay plates and took their sum. For example if CLONE1 appeared on 3 different assay plates with ranks of 78, 79 and 83, the rank sum would be 240.
4. We calculated the p-value (statistical significance) for the rank sum using the null hypothesis that the ranks for CLONE1 were chosen uniformly at random on each assay plate.

Example 10

Additional High throughput Screening of Five Prime Therapeutics' Secreted Protein Library In the high throughput proteoglycan synthesis screen described in Examples 5 and 9, 44 protein plates, representing approximately 3,500 individual secreted proteins, were screened for activity. An additional 16 plates, representing about 1,280 individual secreted proteins, were subsequently screened in a high throughput format for proteoglycan synthesis activity as described in Examples 5 and 9.

The second way of analyzing the screening data from these additional plates of secreted proteins was using a rank sum analysis as described in Example 9, except a probability value of 0.007 was used as the cut-off. Table 1 provides eight novel proteins that gave significant (probability value equal or less than 0.007) anabolic activity in this assay. These proteins, active fragments thereof, and modulators of such proteins are useful in the treatment of arthritis or other human diseases involving altered proteoglycan synthesis. In addition, polynucleotides encoding such proteins, active fragments, and modulators are useful in such treatments.

TABLE 1

Eight novel anabolic hits having p-values of less than 0.007 generated by the high throughput screen described in Example 10

| Clone | p-value (lower) | p-value (upper) | N1 SEQ ID | P1 SEQ ID |
|---|---|---|---|---|
| HG1023575 | 0.9994370 | 0.0011259 | SEQ ID NO: 3 | SEQ ID NO: 4 |
| HG1023576 | 0.9963640 | 0.0048476 | SEQ ID NO: 1 | SEQ ID NO: 2 |
| HG1021695 | 0.957285 | 0.044905 | SEQ ID NO: 5 | SEQ ID NO: 6 |
| HG1021711 | 0.988043 | 0.013114 | SEQ ID NO: 7 | SEQ ID NO: 8 |
| HG1021717 | 0.969211 | 0.032888 | SEQ ID NO: 9 | SEQ ID NO: 10 |
| HG1021734 | 0.962600 | 0.039839 | SEQ ID NO: 11 | SEQ ID NO: 12 |

Table 2 shows the nucleic acid sequences (N1 sequences) of the eight novel anabolic hits.

TABLE 2

N1 Sequences

HG1023576

SEQ ID NO: 1

ATGAGGAACCTACTCTCACCACTCCTCTTCAACATAGTACTGGAAGTCCTAGCCAGAGCAATCA

GACAAAAGAAGGAAATAGAGGAAATCCAAATCGGTAAAGAGGAAGTCAAACTGTCACTGGTTG

CTGACGATATGACCTTTCTCCTTGAGAACCCTACGGACTCCTCTAGAAAAGCTCCTAGAACTGAT

AAAAGAATTCAGCAAAGTTTCCAGATACAAGATTAATGGACACAAATCAGTAGCTCTTCTATACA

TCAACAGCTACCAAGCAGAGAATCACATCAAGAACTCAATCCCTTTTACAATAGCTGCAAAAAAC

AAACAAAAATAA

HG1023575

SEQ ID NO: 3

ATGCTGGTGTCCTCTGAGCTGTTACATTGCTTAATAAAGCTCCTCTTCGTCTTGCTCATCCTCCA

CTTATCTGCATATCTCGTTCTTCCTGGTCACAGGATTAGAACTCAGGACGGGACGAATGGCAAG

GCTAAAAGCTGTAACACAAACAGGGCTGAGACACGCTCCTTGCTCGCCAAGTTGCAGGCGAAG

GGAAGGAAAGAAGAGCTGTGGCCCTTTAGGGAGCCCAGACCTGGGAGCTCCCCGAGCCAGG

GCTATGACCCACTCTTTGGGGCCCTGCGGTTCCTGGCGTCTCCAAGCTTCTGGGGGCCACTGT

GCTCCCTGGTGCCAGCTGTGGAAGTGCTTGCAGTGCGCCTGGTCCAGCTGCAGCCTTATAGA

GAGCCTGCGCCCGGGTACGACCTAGAGCTTCCTACCCCACTGCAGCAACTGGCATGTCTGACT

GCGCAGTGGCCGAACCCCAGGCTCACTCACAAACCCCTCACCACTCCACGCAGTCTCCCTTGG

CAGGCGTGGGATTCAGGCCAGTGGCCTGAATTGAGCGCAGCCTGCCAGGCTGAGTGGGTGGA

ATGA

TABLE 2-continued

N1 Sequences ("HG1021695")
SEQ ID NO: 5
ATGAGGCTTCTCATTCTCACCTGTCTTGTGGCTGTTGCTCTTGCCAGGCCTAAACTTCCTCTTA

GATACCCAGAACGCCTTCAGAATCCATCAGAGAGCAGTGAGCCTATACCATTAGAATCAAGAGA

GGAATACATGAATGGTATGAACAGGCAGAGAAACATTCTGAGAGAAAAACAGACTGATGAAATC

AAGAACTGTGTTGTGGCAGAGCCTGAGAAGATGGAATCCAGCATCAGTTCATCGAGTGAGGAA

CAGTTTTGTAGACTGAACGAATACAACCAACTTCAGCTGCAAGCTGCCCATGCCCAGGAGCAAA

TTCGCAGAATGAATGAAAACAGCCATGTCCAAGTGCCTTTCCAGCAGCTCAACCAACTTGCTGC

CTACCCCTATGCTGTTTGGTACTATCCACAAATCATGCAGTATGTTCCTTTCCCACCGTTTTCCG

ACATCTCCAATCCCACTGCTCATGAAAATTATGAAAAAAATAACGTCATGCTACAGTGG ("HG1021711")
SEQ ID NO: 7
ATGGCGCAGCTGTGCGGGCTGAGGCGGAGCCGGGCGTTTCTCGCCCTGCTGGGATCGCTGC

TCCTCTCTGGGGTCCTGGCGGCCGACCGAGAACGCAGCATCCACGACTTCTGCCTGGTGTCG

AAGGTGGTGGGCAGATGCCGGGCCTCCATGCCTAGGTGGTGGTACAATGTCACTGACGGATC

CTGCCAGCTGTTTGTGTATGGGGGCTGTGACGGAAACAGCAATAATTACCTGACCAAGGAGGA

GTGCCTCAAGAAATGTGCCACTGTCACAGAGAATGCCACGGGTGACCTGGCCACCAGCAGGA

ATGCAGCGGATTCCTCTGTCCCAAGTGCTCCCAGAAGGCAGGATTCTGAAGACCACTCCAGCG

ATATGTTCAACTATGAAGAATACTGCACCGCCAACGCAGTCACTGGGCCTTGCCGTGCATCCTT

CCCACGCTGGTACTTTGACGTGGAGAGGAACTCCTGCAATAACTCCATGGTCTACCTGATCCG

GGTGGCACGGAGGAACCAGGAGCGTGCCCTGCGCACCGTCTGGAGCTCCGGAGATGACAAG

GAGCAGCTGGTGAAGAACACATATGTCCTG ("HG1021717")
SEQ ID NO: 9
ATGAATCCTGCGGCAGAAGCCGAGTTCAACATCCTCCTGGCCACCGACTCCTACAAGGTTACT

CACTATAAACAATATCCACCCAACACAAGCAAAGTTTATTCCTACTTTGAATGCCGTGAAAAGAA

GACAGAAAACTCCAAATTAAGGAAGGTGAAATATGAGGAAACAGTATTTTATGGGTTGCAGTAC

ATTCTTAATAAGTACTTAAAAGGTAAAGTAGTAACCAAAGAGAAAATCCAGGAAGCCAAAGATGT

CTACAAAGAACATTTCCAAGATGATGTCTTTAATGAAAAGGGATGGAACTACATTCTTGAGAAGT

ATGATGGGCATCTTCCAATAGAAATAAAAGCTGTTCCTGAGGGCTTTGTCATTCCCAGAGGAAA

TGTTCTCTTCACGGTGGAAAACACAGATCCAGAGTGTTACTGGCTTACAAATTGGATTGAGACT

ATTCTTGTTCAGTCCTGGTATCCAATCACAGTGGCCACAAATTCTAGAGAGCAGAAGAAAATATT

GGCCAAATATTTGTTAGAAACTTCTGGTAACTTAGATGGTCTGGAATACAAGTTACATGATTTG

GCTACAGAGGAGTCTCTTCCCAAGAGTACCATAACAGCTTGGGGAAAGACCATGA ("HG1021734")
SEQ ID NO: 11
ATGGTTCGTCTGCCTCTGCAGTGCGTCCTCTGGGGCTGCTTGCTGACCGCTGTCCATCCAGAA

CCACCCACTGCATGCAGAGAAAAACAGTACCTAATAAACAGTCAGTGCTGTTCTTTGTGCCAGC

CAGGACAGAAACTGGTGAGTGACTGCACAGAGTTCACTGAAACGGAATGCCTTCCTTGCGGTG

AAAGCGAATTCCTAGACACCTGGAACAGAGAGACACACTGCCACCAGCACAAATACTGCGACC

CCAACCTAGGGCTTCGGGTCCAGCAGAAGGGCACCTCAGAAACAGACACCATCTGCACCTGTG

AAGAAGGCTGGCACTGTACGAGTGAGGCCTGTGAGAGCTGTGTCCTGCACCGCTCATGCTCG

TABLE 2-continued

N1 Sequences

CCCGGCTTTGGGGTCAAGCAGATTGCTGTGAGACCAAAGACCTGGTTGTGCAACAGGCAGGC

ACAAACAAGACTGATGTTGTCTGTGGTGAGTCCTGGACAATGGGCCCTGGAGAAAGCC

Table 3 provides the amino acid sequences (P1 sequences) encoded by the corresponding nucleic acid sequences of Table 2. The N1 and P1 sequences are correlated as shown in Table 2.

TABLE 3

P1 sequences

HG1023576
SEQ ID NO: 2
MRNLLSPLLFNIVLEVLARAIRQKKEIEEIQIGKEEVKLSLVADDMTFLLENPTDSSRKLLELIK

EFSKVSRYKINGHKSVALLYINSYQAENHIKNSIPFTIAAKNKQK

HG1023575
SEQ ID NO: 4
MLVSSELLHCLIKLLFVLLILHLSAYLVLPGHRIRTQDGTNGKAKSCNTNRAETRSLLAKLQAKG

RKEELWPFREPRPGSSPSQGYDPLFGALRFLASPSFWGPLCSLVPAVEVLAVRLVQLQPYREPAP

GYDLELPTPLQQLACLTAQWPNPRLTHKPLTTPRSLPWQAWDSGQWPELSAACQAEWVE ("HG1021695")
SEQ ID NO: 6
MRLLI LTCLVAVALARPKLPLRYPERLQNPSESSEPIPLESREEYMNGMNRQRNILREKQTDEI

KNCVVAEPEKMESSISSSSEEQFCRLNEYNQLQLQAAHAQEQIRRMNENSHVQVPFQQLNQLAAY

PYAVWYYPQIMQYVPFPPFSDISNPTAHENYEKNNVMLQW ("HG1021711")
SEQ ID NO: 8
MAQLCGLRRSRAFLALLGSLLLSGVLAADRERSIHDFCLVSKVVGRCRASMPRVVWYNVTDGSCQ

LFVYGGCDGNSNNYLTKEECLKKCATVTENATGDLATSRNAADSSVPSAPRRQDSEDHSSDMFNY

EEYCTANAVTGPCRASFPRVVYFDVERNSCNNSMVYLIRVARRNQERALRTVVVSSGDDKEQLVK

NTYVL ("HG1021717")
SEQ ID NO: 10
MNPAAEAEFNILLATDSYKVTHYKQYPPNTSKVYSYFECREKKTENSKLRKVKYEETVFYGLQYI

LNKYLKGKVVTKEKIQEAKDVYKEHFQDDVFNEKGWNYILEKYDGHLPIEIKAVPEGFVIPRGNV

LFTVENTDPECYWLTNWIETILVQSWYPITVATNSREQKKILAKYLLETSGNLDGLEYKLHDFGY

RGVSSQEYHNSLGERP ("HG1021734")
SEQ ID NO: 12
MVRLPLQCVLWGCLLTAVHPEPPTACREKQYLINSQCCSLCQPGQKLVSDCTEFTETECLPCGES

EFLDTWNRETHCHQHKYCDPNLGLRVQQKGTSETDTICTCEEGWHCTSEACESCVLHRSCSPGFG

VKQIAVRPKTWLCNRQAQTRLMLSVVSPGQWALEKA

The invention claimed is:

1. A pharmaceutical composition for treating osteoarthritis in a subject comprising at least a first therapeutic agent and a pharmaceutically acceptable carrier, wherein the first therapeutic agent comprises an isolated polypeptide with an amino acid sequence that is at least 95% identical to SEQ ID NO 4, and wherein said polypeptide stimulates proteoolycan synthesis in chondrocytes.

2. A pharmaceutical composition for treating arthritis in a subject comprising at least a first therapeutic agent and a pharmaceutically acceptable carrier, wherein the first therapeutic agent comprises an isolated polypeptide with the amino acid of SEQ ID NO: 4.

3. The pharmaceutical composition of claim 1, wherein the first therapeutic agent comprises a polypeptide with the amino acid sequence of SEQ ID NO 4.

* * * * *